US012569113B2

(12) United States Patent
Tani

(10) Patent No.: US 12,569,113 B2
(45) Date of Patent: Mar. 10, 2026

(54) MEDICAL SYSTEM, PROCESSING PROTOCOL CONTROL METHOD, AND SIGNAL PROCESSING DEVICE

(71) Applicant: OLYMPUS CORPORATION, Tokyo (JP)

(72) Inventor: Shinsuke Tani, Akiruno (JP)

(73) Assignee: OLYMPUS CORPORATION, Tokyo (JP)

( * ) Notice: Subject to any disclaimer, the term of this patent is extended or adjusted under 35 U.S.C. 154(b) by 500 days.

(21) Appl. No.: 18/104,827

(22) Filed: Feb. 2, 2023

(65) Prior Publication Data

US 2023/0172426 A1 Jun. 8, 2023

Related U.S. Application Data

(63) Continuation of application No. PCT/JP2020/030157, filed on Aug. 6, 2020.

(51) Int. Cl.
*A61B 1/00* (2006.01)
(52) U.S. Cl.
CPC ...... *A61B 1/00009* (2013.01); *A61B 1/00006* (2013.01); *A61B 1/00016* (2013.01); *A61B 1/00045* (2013.01); *A61B 1/00087* (2013.01)
(58) Field of Classification Search
CPC ............ A61B 1/00009; A61B 1/00006; A61B 1/00016; A61B 1/00011; A61B 1/045; A61B 1/0655
See application file for complete search history.

(56) References Cited

U.S. PATENT DOCUMENTS 8,830,310 B2 * 9/2014 Mitsuhashi ............ A61B 1/041
600/109
2006/0116552 A1 * 6/2006 Noguchi ................ A61B 1/121
600/132

(Continued)

FOREIGN PATENT DOCUMENTS

CA 2657614 A1 1/2008
CA 2875651 A1 12/2013

(Continued)

OTHER PUBLICATIONS

International Search Report dated Oct. 20, 2020 issued in PCT/JP2020/030157.

*Primary Examiner* — Anh Tuan T Nguyen
*Assistant Examiner* — Jae Wool
(74) *Attorney, Agent, or Firm* — Scully, Scott, Murphy & Presser, P.C.

(57) ABSTRACT

A medical system includes an imager configured to pick up an image and output an image signal, a signal processing device configured to generate an observation image from the image signal, a display configured to display the observation image, and a relay device, and the signal processing device derives a processing sequence that minimizes a time duration from when the imager picks up an image until the display displays the observation image, based on a first specification of the image signal at the imager, a second specification of the signal processing device, a third specification of the observation image at the display, and a communication protocol of the relay device, provides instruction of a fourth specification to the imager based on the processing sequence, and provides instruction of a fifth specification to the display based on the processing sequence.

19 Claims, 12 Drawing Sheets

(56) References Cited

U.S. PATENT DOCUMENTS

| 2011/0317017 A1* | 12/2011 | Shin ..................... H04W 72/12 |
| | | 348/E7.085 |
| 2013/0054467 A1* | 2/2013 | Dala .................. G06F 21/6245 |
| | | 705/51 |
| 2014/0340496 A1* | 11/2014 | Okawa .............. A61B 1/00009 |
| | | 600/103 |
| 2018/0109852 A1* | 4/2018 | Mandapaka ........ H04W 12/068 |
| 2020/0053186 A1* | 2/2020 | Kiyoshige ............. H04W 48/16 |
| 2021/0105467 A1* | 4/2021 | Tani ...................... H04N 7/183 |
| 2021/0121047 A1* | 4/2021 | Tani .................. A61B 1/00016 |
| 2021/0182656 A1* | 6/2021 | Furukawa ........... G06N 3/0464 |
| 2021/0195115 A1* | 6/2021 | Tani .................. A61B 1/00036 |
| 2022/0338717 A1* | 10/2022 | Kimura ........... A61B 1/000095 |
| 2023/0100302 A1* | 3/2023 | Asai ...................... G16H 30/20 |
| | | 705/2 |
| 2023/0301489 A1* | 9/2023 | Nomura ............. A61B 1/00009 |

FOREIGN PATENT DOCUMENTS

| EP | 1652464 | A1 | 5/2006 |
| JP | 2005118159 | A | 5/2005 |
| JP | 2005182670 | A | 7/2005 |
| JP | 2008284037 | A | 11/2008 |
| JP | 2010532636 | A | 10/2010 |
| JP | 2018510430 | A | 4/2018 |
| JP | 2019023646 | A | 2/2019 |
| JP | 2019082815 | A | 5/2019 |
| JP | 2020504404 | A | 2/2020 |
| WO | 2005077250 | A1 | 8/2005 |
| WO | 2013184226 | A1 | 12/2013 |

* cited by examiner

FIG. 8

MEDICAL SYSTEM, PROCESSING PROTOCOL CONTROL METHOD, AND SIGNAL PROCESSING DEVICE

CROSS REFERENCE TO RELATED APPLICATION

This application is a continuation application of PCT/JP2020/030157 filed on Aug. 6, 2020, the entire contents of which are incorporated herein by this reference.

BACKGROUND OF THE INVENTION

1. Field of the Invention

An embodiment of the present invention relates to a medical system, a processing protocol control method, and a signal processing device.

2. Description of the Related Art

Medical diagnosis using an electronic endoscope is performed in medical fields. In such an electronic endoscope (hereinafter referred to as an endoscope), an image pickup device such as a CCD is built in at a distal end of an insertion portion that is inserted into a body. An image pickup signal acquired by the CCD is inputted to a processor and provided with image development processing. Specifically, the processor generates an endoscope image by providing signal processing or the like on the inputted image pickup signal. The endoscope image generated by the processor is outputted to a display device such as a monitor and displayed. Accordingly, an image (endoscope image) of the inside of the body of an examinee, such as the stomach or the intestine can be observed.

Typically, the endoscope and the processor are connected through a signal cable. Such an endoscope system has problems such as interference with the signal cable when the endoscope is operated and difficulty to carry. Thus, what is called a wireless endoscope system configured to wirelessly perform signal transmission and reception between the endoscope and the processor has been disclosed.

Typically, an endoscope system mainly constituted by the endoscope, the processor, and the display device has been used and optimized as a stand-alone system that operates independently from networks.

Recently, a demand for a remote medical care such as a remote pathological diagnosis has been increasing. To meet the demand, a network medical system has been disclosed in which what is called medical images acquired by an image pickup apparatus, such as an image-pickup image inside the body of a subject and an image-pickup image of a pathological sample are transmitted to a diagnostic device and a display device through a network such as the Internet (for example, Japanese Patent Application Laid-Open Publication No. 2005-182670 and Japanese Patent Application Laid-Open Publication No. 2019-82815).

The endoscope, the processor, and the display device are connected through a network when the endoscope system is established as a network medical system.

SUMMARY OF THE INVENTION

A medical system according to an aspect of the present invention includes an image pickup instrument configured to output an image pickup signal acquired by picking up an image of an object, a signal processing device configured to generate an observation image from the image pickup signal, at least one display device configured to display the observation image, and a relay device configured to connect the image pickup instrument, the signal processing device, and the display device. The signal processing device derives a processing sequence that minimizes a time duration from when the image pickup instrument picks up an image of an object until the display device displays the observation image, based on a first processing specification of the image pickup signal at the image pickup instrument, a second processing specification of the signal processing device, a third processing specification of the observation image at the display device, and a communication protocol of the relay device. The signal processing device provides instruction of a fourth processing specification to the image pickup instrument based on the processing sequence and provides instruction of a fifth processing specification to the display device based on the processing sequence.

A processing protocol control method according to another aspect of the present invention includes: pairing an image pickup instrument, a signal processing device, and a display device through a communication line including a relay device, the image pickup instrument being configured to output an image pickup signal acquired by picking up an image of an object, the signal processing device being configured to generate an observation image from the image pickup signal, the display device being configured to display the observation image; deriving, by the signal processing device, a processing sequence that minimizes a time duration from when the image pickup instrument picks up an image of an object until the display device displays the observation image, based on a first processing specification of the image pickup signal at the image pickup instrument, a second processing specification of the signal processing device, a third processing specification of the observation image at the display device, and a communication protocol of the relay device; providing instruction of a fourth processing specification from the signal processing device to the image pickup instrument based on the processing sequence; and providing instruction of a fifth processing specification from the signal processing device to the display device based on the processing sequence.

A signal processing device according to another aspect of the present invention includes a reception circuit configured to receive an image pickup signal from an image pickup instrument through a relay device, a transmission circuit configured to transmit an observation image to a display device through the relay device, a memory, and a processor including hardware. The processor detects a first processing specification of the image pickup signal at the image pickup instrument, a second processing specification of the signal processing device, a third processing specification of the observation image at the display device, and a communication protocol of the relay device and stores the first processing specification, the second processing specification, the third processing specification, and the communication protocol in the memory. The processor derives a processing sequence of a condition that a time duration from when the image pickup instrument picks up an image of an object until the display device displays the observation image is minimized, based on each of the first processing specification, the second processing specification, the third processing specification, and the communication protocol of the relay device, which are stored in the memory. The signal processing device provides instruction of a fourth processing specification to the image pickup instrument based on the processing sequence and the signal processing device provides instruction of a fifth processing specification to the display device based on the processing sequence.

BRIEF DESCRIPTION OF THE DRAWINGS

FIG. 8 is a time chart for description of a processing sequence related to an endoscope image;

DETAILED DESCRIPTION OF THE PREFERRED EMBODIMENTS

An embodiment will be described below with reference to the accompanying drawings.

Figure 1:
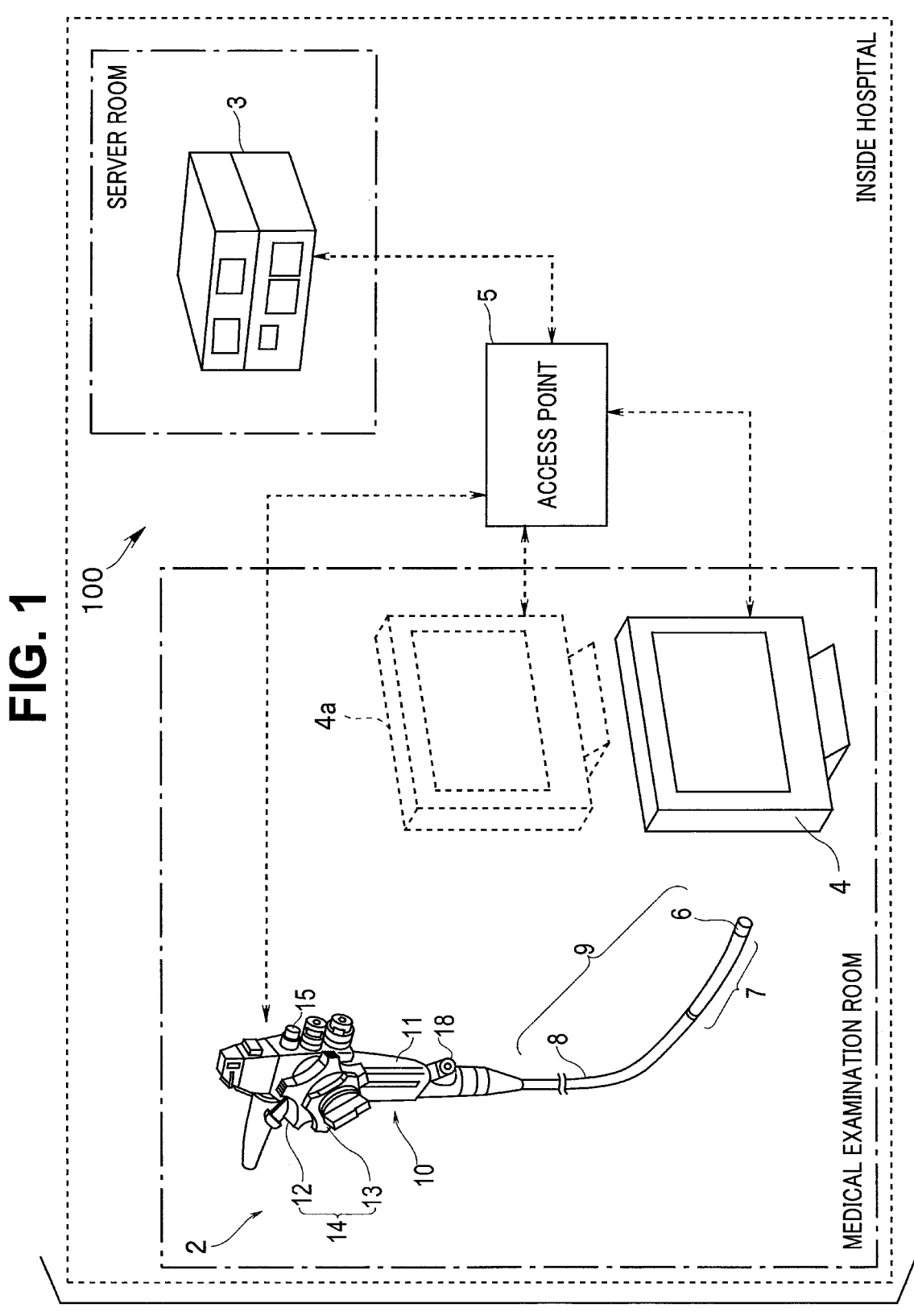
FIG. 1 is a diagram for description of an example of an entire configuration of a medical system according to an embodiment of the present invention.

FIG. 1 is a diagram for description of an example of an entire configuration of a medical system 100 according to the embodiment of the present invention. The medical system 100 includes an endoscope 2, an image processing server 3, a display device 4, and an access point 5 that is a relay device (relay point). The medical system 100 is a system established in a hospital. The endoscope 2 and the display device 4 are disposed in a medical examination room. The image processing server 3 is disposed in a server room.

The endoscope 2, the image processing server 3, and the display device 4 can communicate data with one another through the access point 5. The endoscope 2 and the access point 5 perform communication in a wireless or wired manner. The image processing server 3 and the access point 5 perform communication in a wireless or wired manner. The display device 4 and the access point 5 perform communication in a wireless or wired manner. Wireless communication utilizes a scheme compliant with, for example, IEEE802.11 as a wireless LAN (local area network) standard, a scheme compliant with 5G and Local 5G as mobile communication standards, or the like. Note that a communication scheme is not limited thereto but may be, for example, a next-generation communication standard.

The endoscope 2 as an image pickup instrument includes an elongated insertion portion 9 and an operation portion 10. The insertion portion 9 of the endoscope 2 includes, sequentially from a distal end, a distal end portion 6, a bending portion 7, and a flexible tube portion 8. A solid-state image pickup device is disposed in the distal end portion 6, and the solid-state image pickup device photoelectrically converts an object image and outputs an image pickup signal. The endoscope 2 wirelessly transmits the image pickup signal to the image processing server 3. The endoscope 2 may transmit, to the image processing server 3, a signal having communication quality improved by performing compression processing or the like on the image pickup signal. Specifically, the image pickup signal transmitted from the endoscope 2 is transmitted to the image processing server 3 through the access point 5.

The operation portion 10 is provided with a bending operation portion 14 for performing an operation to bend the bending portion 7 of the insertion portion 9, and switches such as a scope switch 15 for achieving various kinds of functions. In the bending operation portion 14, a UD bending operation knob 12 for performing an operation to bend the bending portion 7 in an up-down direction and an RL bending operation knob 13 for performing an operation to bend the bending portion 7 in a right-left direction are disposed over each other. The scope switch 15 includes a plurality of switches. For example, the plurality of switches are switches for controlling processing at the image processing server 3, such as start and stop of video recording, and switches for controlling processing at a predetermined site of the endoscope 2, such as light source switching to NBI (narrow band imaging). With the scope switch 15, a user can control various instruments connected to the endoscope 2 through a network.

A coupling part of the insertion portion 9 and the operation portion 10 includes a grasping portion 11 and an opening 18 of a treatment instrument channel that allows insertion of the insertion portion 9, the opening 18 being disposed at a bend preventing portion provided between the grasping portion 11 and one end of the flexible tube portion 8 of the insertion portion 9.

The image processing server 3 generates an image signal by performing image development processing on the image pickup signal received from the endoscope 2. When having received a signal provided with compression processing or the like, the image processing server 3 generates an image signal by performing processing (for example, decompression processing on the signal provided with the compression processing) based on the received signal. The image signal is wirelessly transmitted to the display device 4 through the access point 5.

The image processing server 3 optimizes a processing process so that a delay time duration from image pickup to display is minimized, based on a processing specification (a transmission-reception frame rate, a processing frame rate, and a communication protocol) of each of the endoscope 2, the access point 5, and the display device 4.

A standard processing specification of the endoscope 2 is referred to as a first processing specification, a standard processing specification of the image processing server 3 is referred to as a second processing specification, and a standard processing specification of the display device 4 is referred to as a third processing specification. In addition, a standard frame rate of the endoscope 2 is referred to as a first frame rate, a standard frame rate of the image processing server 3 is referred to as a second frame rate, and a standard frame rate of the display device 4 is referred to as a third frame rate. Note that the standard processing specification and the standard frame rate are a processing specification and a frame rate when each device is independently used.

In the optimized processing process, a frame rate of the endoscope 2 is referred to as a fourth frame rate, and a frame rate of the display device 4 is referred to as a fifth frame rate.

The display device 4 is display means in the medical system 100 and corresponds to a display device outside the endoscope 2 and the image processing server 3. The display device 4 has a network function and displays, as an endoscope image, an image signal received from the image processing server 3. The display device 4 is, for example, a notebook PC, a tablet, or a smartphone. A display having no network function may be used as the display device 4 with connection to a wireless instrument.

The display device 4 includes a display 41, a communication control circuit 42, a recording medium 43, a receiver 44, and a transmitter 45.

The display 41 displays an endoscope image received from the image processing server 3. The display 41 is, for example, a liquid crystal display, an organic EL (electroluminescence) display, or a CRT (cathode ray tube) display.

The communication control circuit 42 controls operation of the entire display device 4 based on a processing specification transmitted from the image processing server 3. The communication control circuit 42 controls speed of display of an endoscope image on the display 41. The communication control circuit 42 transmits the processing specification of the display device 4 in accordance with a request from the image processing server 3.

The recording medium 43 records an endoscope image transmitted from the image processing server 3 and stores various parameters necessary for setting of the display device 4.

The receiver 44 receives an endoscope image transmitted from the image processing server 3 and processing specification data related to processing specifications through the access point 5. The received endoscope image and processing specification data are outputted to the communication control circuit 42.

The transmitter 45 wirelessly transmits, for example, the processing specification of the display device 4, which is outputted from the communication control circuit 42.

The medical system 100 of the present embodiment may include a plurality of display devices 4 and 4a. An endoscope image may be displayed on all display devices 4 and 4a or on one selected display device 4. Any of the display devices 4 and 4a may be installed in a room other than the medical examination room in which the endoscope 2 is disposed.

Figure 2:
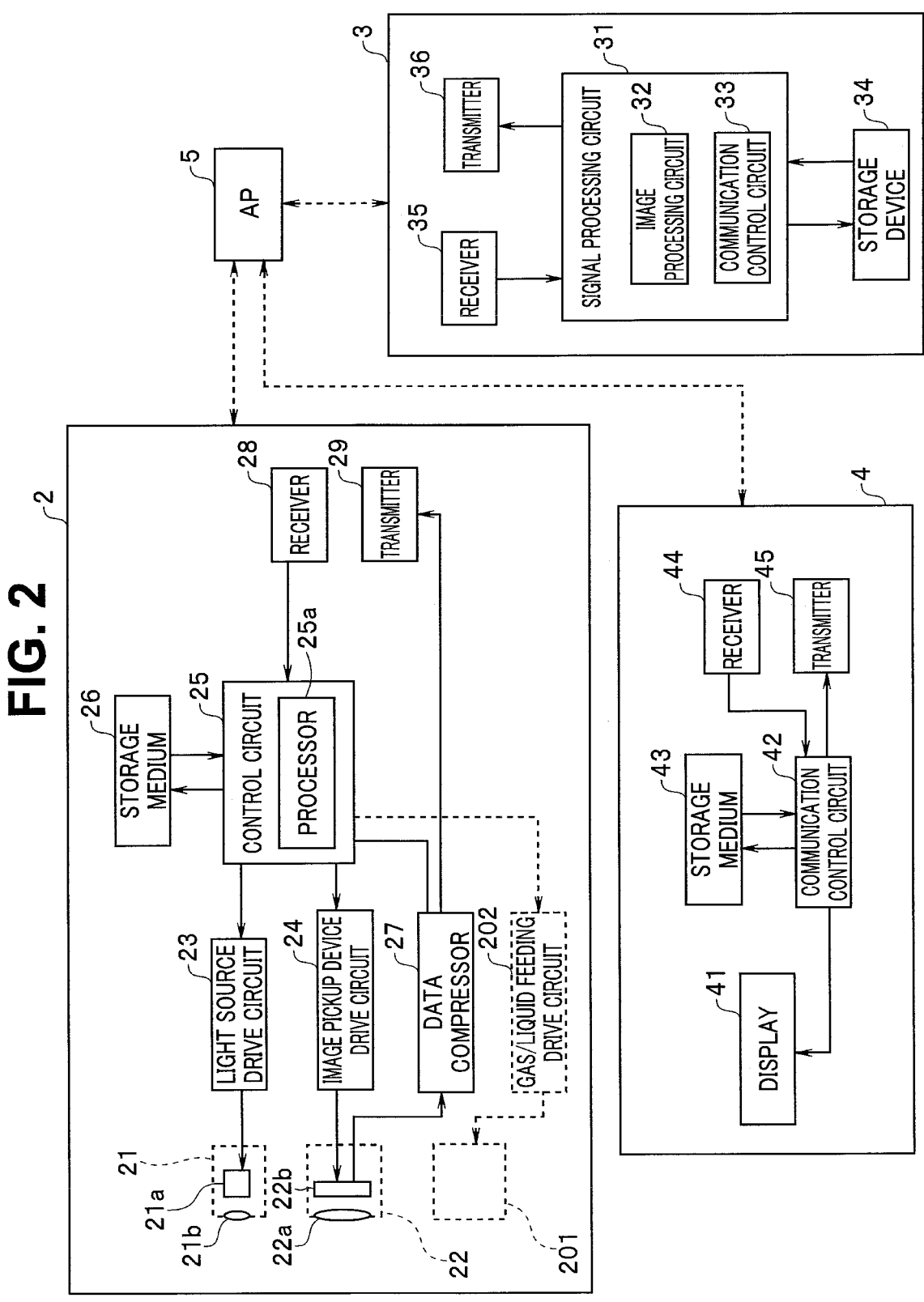
FIG. 2 is a block diagram illustrating an example of a hardware configuration of the medical system.

FIG. 2 illustrates a configuration for performing processing related to a processing protocol control method of the embodiment in a hardware configuration of the medical system.

The endoscope 2 includes a light source 21 and an image pickup unit 22 in the distal end portion 6. The endoscope 2 also includes a light source drive circuit 23, an image pickup device drive circuit 24, a control circuit 25, a storage medium 26, a data compressor 27, a receiver 28, and a transmitter 29 in the operation portion 10.

The light source 21 includes a light-emitting element 21a and an illumination optical system 21b.

The light-emitting element 21a includes, for example, an LED. The light-emitting element 21a generates illumination light having a light quantity in accordance with a light-emitting element drive signal supplied from the light source drive circuit 23.

The illumination optical system 21b is configured as, for example, an optical system including an illumination lens. The illumination optical system 21b irradiates an object outside the distal end portion 6 with the illumination light emitted from the light-emitting element 21a.

The image pickup unit 22 is a camera including an observation optical system 22a and an image pickup device 22b.

The observation optical system 22a is an optical system including an imaging lens. The observation optical system 22a on which return light (reflected light) emitted from the object in accordance with irradiation with the illumination light from the light source 21 is incident images the return light on an imaging plane of the image pickup device 22b.

The image pickup device 22b includes an image sensor such as a CCD or a CMOS image sensor. The image pickup device 22b drives in accordance with an image pickup device drive signal supplied from the image pickup device drive circuit 24. The image pickup device 22b generates an image pickup signal through image pickup of the return light imaged by the observation optical system 22a. Then, the image pickup device 22b outputs the generated image pickup signal (RAW image data) to the data compressor 27. Specifically, the endoscope 2 acquires the RAW image data by picking up an image of inside of a subject with the image pickup unit 22 provided at the distal end portion 6 of the insertion portion 9. Note that the RAW image data is image data in which information of light at image pickup is held intact without adjustment. In other words, the RAW image data is pre-fabrication image data provided with neither demosaic processing nor the like.

The light source drive circuit 23 outputs, in accordance with control by the control circuit 25, a light-emitting element drive signal that drives the light-emitting element 21a.

The image pickup device drive circuit 24 outputs, in accordance with control by the control circuit 25, an image pickup device drive signal that drives the image pickup device 22b.

The control circuit 25 is constituted by one or more processors 25a such as a central processing unit (hereinafter referred to as a "CPU"). The control circuit 25 controls operation of the entire endoscope 2. Specifically, the control circuit 25 controls operation of the endoscope 2 based on an instruction/input at a non-illustrated input device and outputs a control signal/setting signal to each component. As described later, the control circuit 25 instructs operation to the image pickup device drive circuit 24 and the data compressor 27 based on the third processing specification transmitted from the image processing server 3.

The storage medium 26 is, for example, a flash memory or a ROM (read-only memory). The storage medium 26 stores a program used to control each component of the endoscope 2 and various kinds of programs corresponding to operation of the control circuit 25.

The data compressor 27 compresses and encodes the RAW image data outputted from the image pickup device 22b in accordance with control by the control circuit 25. In the medical system 100, an image pickup signal acquired at the endoscope 2 is wirelessly transmitted to the image processing server 3. The larger an amount of data transmitted from the endoscope 2 to the image processing server 3 is, the longer a transmission time duration gets, which potentially causes delay of image processing. Therefore, the endoscope 2 compresses the RAW image data to a data amount appropriate for image processing performance of the image processing server 3 and transmits the RAW image data at an appropriate timing. The data compressor 27 compresses and encodes the RAW image data inputted from the image pickup device 22b at a compression ratio designated by the control circuit 25.

Note that advantages of transmission of the RAW image data from the endoscope 2 to the image processing server 3 are as follows. The RAW image data has a data amount smaller than a data amount of image data after typical demosaic processing, and thus a load due to compression and transmission is smaller. As a result, low-latency transmission is achieved. Moreover, the RAW image data is data in which information of light at image pickup is held intact without adjustment, and is data with less degradation of image quality. As a result, adjustment of color, brightness, and the like can be performed at the image processing server 3 without degradation of image quality.

The receiver 28 receives the third processing specification (specification data) transmitted from the image processing server 3 through the access point 5 (AP 5). The received specification data is outputted to the control circuit 25.

The transmitter 29 wirelessly transmits the compressed and encoded RAW image data that is outputted from the data compressor 27.

The endoscope 2 has a gas/liquid feeding function to remove grime on the observation optical system 22a. The endoscope 2 includes a gas/liquid feeding unit 201 and a gas/liquid feeding drive circuit 202 so that gas such as carbon dioxide and liquid such as water can be fed. The gas/liquid feeding unit 201 ejects gas and liquid supplied from a non-illustrated gas/liquid feeding source, from the distal end portion 6 in accordance with control by the gas/liquid feeding drive circuit 202. The gas/liquid feeding drive circuit 202 generates and outputs, in accordance with control by the control circuit 25, a drive signal for ejecting liquid and gas from the gas/liquid feeding unit 201.

The image processing server 3 as a signal processing device includes a signal processing circuit 31, a storage device (memory) 34, a receiver 35, and a transmitter 36.

The signal processing circuit 31 controls operation of the entire image processing server 3 and performs various kinds of processing on a signal received from outside. The signal processing circuit 31 includes an image processing circuit 32 and a communication control circuit 33.

The image processing circuit 32 is an integrated circuit such as an FPGA (field programmable gate array). The signal processing circuit 31 generates an endoscope image by performing predetermined signal processing such as demosaic processing on RAW image data transmitted from the endoscope 2 and transmits the generated endoscope image to the display device 4. The image processing circuit 32 performs, for example, image development processing on the RAW image data.

All or part of the processing at the image processing circuit 32 may be performed by a software program. Specifically, a non-illustrated processor provided in the signal processing circuit 31 may perform, for example, the same processing and operation as the image processing circuit 32 by executing a program read from the storage device 34.

The communication control circuit 33 is configured as an integrated circuit such as an FPGA (field programmable gate array). Note that all or part of processing at the communication control circuit 33 may be performed by a software program. Specifically, the non-illustrated processor provided in the signal processing circuit 31 may perform, for example, the same processing and operation as the communication control circuit 33 by executing a program read from the storage device 34.

The communication control circuit 33 performs pairing with the endoscope 2 and the display device 4 and optimizes a processing sequence from acquisition of an image pickup signal (RAW image data) at the image pickup device 22b to display of an endoscope image at the display device 4.

Specifically, the communication control circuit 33 optimizes the processing sequence with taken into account a transmission frame rate of the endoscope 2, a display frame rate of the display device, a transmission-reception frame rate and a communication protocol of a relay device (the access point 5 in the case of FIG. 1) on a communication path between the endoscope 2 and the image processing server 3, a transmission-reception frame rate and a communication protocol of a relay device (the access point 5) on a communication path between the image processing server 3 and the display device 4, a transmission-reception frame rate of the image processing server 3, and a frame rate of signal processing at the image processing circuit 32. Note that these frame rates and communication protocols are stored in a non-illustrated storage medium (such as a flash memory or a ROM) of the communication control circuit 33 or the storage device 34 in advance.

The processing sequence optimization at the communication control circuit 33 will be described below with examples of specific processing sequences. FIGS. 3 to 6 and 8 to 11 are each a time chart for description of a processing sequence related to an endoscope image. In FIGS. 3 to 6 and 8 to 11, a horizontal axis represents time t, and a plurality of lanes provided in a vertical direction represent a series of processes from acquisition of an image pickup signal at the image pickup device 22b to display of an endoscope image at the display device 4.

Specifically, processes of image pickup (1), compression (2), transmission (3), reception (4), transmission (5), reception (6), image processing (7), transmission (8), reception (9), transmission (10), reception (11), and display (12) are illustrated sequentially from an uppermost lane. Note that a rectangle in each lane represents a time duration in which data of one frame (=one endoscope image) is processed. The endoscope 2 picks up a moving image made of a plurality of endoscope images photographed at a predetermined frame rate.

Image pickup (1) is processing of picking up an image of an object at the image pickup device 22b of the endoscope 2. Compression (2) is compression processing at the data compressor 27 of the endoscope 2. Transmission (3) is processing of data transmission from the transmitter 29 of the endoscope 2. Reception (4) is data reception processing at the access point 5. Transmission (5) is data transmission processing at the access point 5. Reception (6) is data reception processing at the receiver 35 of the image processing server 3. Image processing (7) is image processing at the image processing circuit 32 of the image processing server 3. Transmission (8) is data transmission processing at the transmitter 36 of the image processing server 3. Reception (9) is data reception processing at the access point 5. Transmission (10) is data transmission processing at the access point 5. Reception (11) is data reception processing at the receiver 44 of the display device 4. Display (12) is image display processing at the communication control circuit 42 of the display device 4.

FIGS. 3 to 6 and 8 to 11 each illustrate a time chart of n frames (for example, n=3) continuous from a frame (first frame) acquired first after the image pickup device 22b starts image pickup of the object. In reality, processing is continuously performed on an (n+1)-th frame and later for a duration until the image pickup ends. In FIGS. 3 to 6 and 8 to 11, processing flow of image data of the first frame is illustrated with arrows.

(1) Case in which Processing Performance of the Endoscope 2 is Low

First, processing sequence optimization when processing performance of the endoscope 2 is lower than processing performance of the image processing server 3 will be described below with reference to FIGS. 3 and 4.

A case in which the processing performance of the endoscope 2 is 30 fps (frames per second) and the processing performance of the image processing server 3 and processing performance of the display device 4 are 60 fps will be described below. FIG. 3 corresponds to an example of the processing sequence before optimization, and FIG. 4 corresponds to an example of a processing sequence obtained by optimizing the sequence illustrated in FIG. 3.

Figure 3:
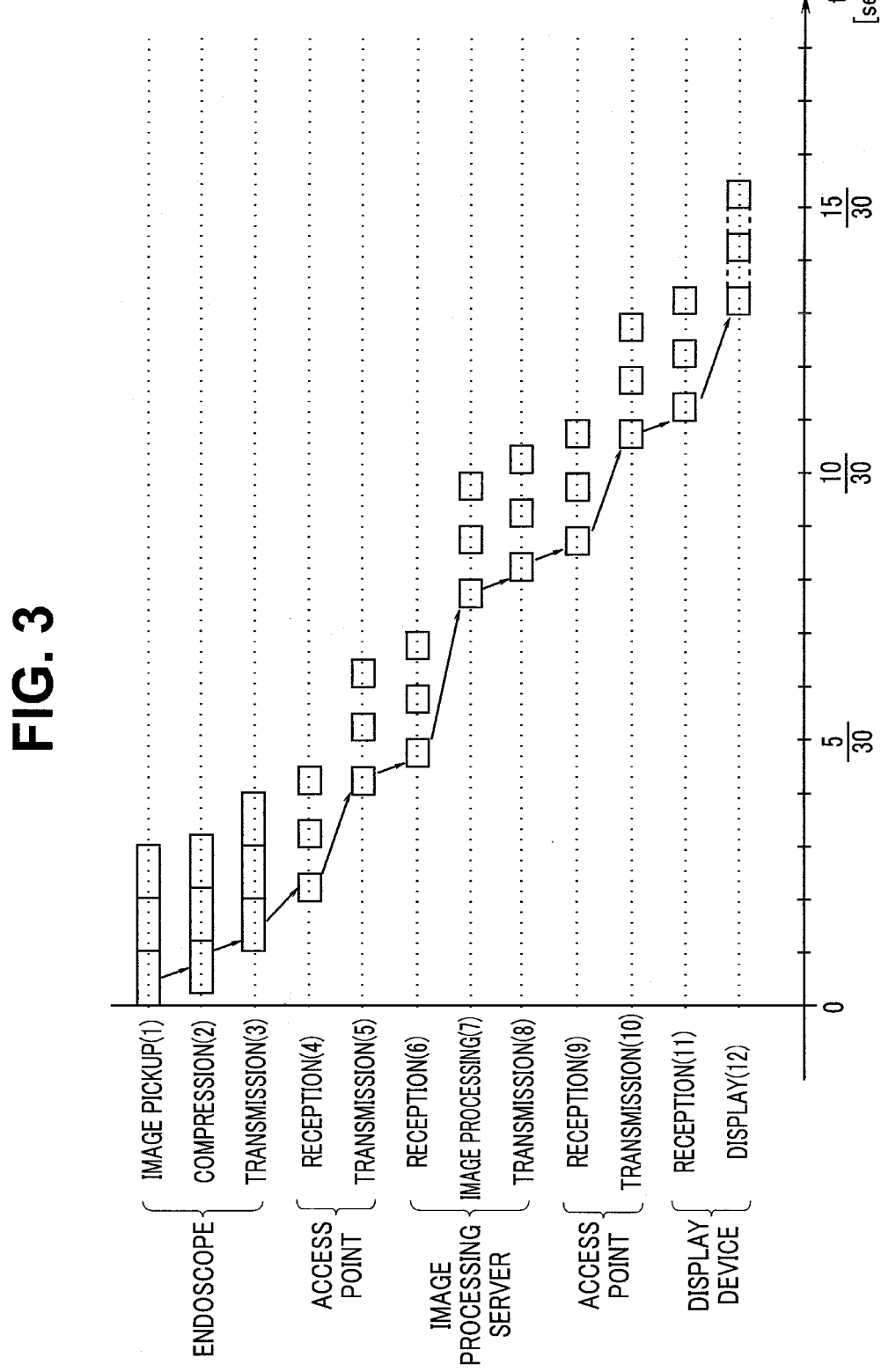
FIG. 3 is a time chart for description of a processing sequence related to an endoscope image.

<Processing Sequence of FIG. 3>

The processing sequence illustrated in FIG. 3 will be described first. An image of the object is picked up at the image pickup device 22b of the endoscope 2. Since the processing performance of the endoscope 2 is 30 fps, the image pickup device 22b acquires image pickup signals of 30 frames in each second. In other words, the image pickup device 22b acquires an image pickup signal of one frame in each ⅓₀ seconds. The acquired image pickup signals (RAW image data) are outputted from the image pickup device 22b to the data compressor 27 without delay.

The data compressor 27 compresses the inputted RAW image data at a predetermined compression ratio and then outputs the compressed data to the transmitter 29. The transmitter 29 wirelessly transmits the RAW image data to the access point 5. The transmitter 29 transmits the RAW image data of one frame in ⅓₀ seconds to the access point 5.

The access point 5 has such performance that the access point 5 can receive RAW image data of 60 frames in each second. The access point 5 receives the RAW image data of one frame transmitted from the transmitter 29 for ⅟₆₀ seconds. The access point 5 transmits the received RAW image data to the image processing server 3.

Note that the medical system illustrated in FIG. 1 corresponds to an example in which one access point 5 exists between the endoscope 2 and the image processing server 3, but in reality, RAW image data transmitted from the endoscope 2 often reaches the image processing server 3 through a plurality of access points. Therefore, in the time charts illustrated in FIGS. 3 to 6 and 8 to 11, "reception (4)" indicates a timing of reception at an access point that receives RAW image data directly from the endoscope 2, and "transmission (5)" indicates a timing of transmission at an access point that lastly transmits RAW image data to the image processing server 3 through a plurality of access points. Accordingly, data delay occurs through a plurality of access points. In FIGS. 3 to 6 and 8 to 11, this delay time duration is, for example, ⅔₀ seconds.

The receiver 35 of the image processing server 3 receives the RAW image data from the access point 5. The receiver 35 receives the RAW image data of one frame transmitted from the access point 5 for ⅟₆₀ seconds. The received RAW image data is inputted to the image processing circuit 32. The image processing circuit 32 starts image development processing after a wait time (for example, ⅗₀ seconds) set in advance has elapsed since the RAW image is inputted. Start timing of the processing is sometimes defined with, for example, the number of accumulated frames instead of the wait time. For example, it may be defined that the processing starts when data of three frames is accumulated in a buffer.

The RAW image data is converted into an endoscope image through the image development processing. Since the processing performance of the image processing server 3 is 60 fps, the image processing circuit 32 can perform image development of RAW image data of 60 frames in each second. However, since RAW image data of one frame is inputted at intervals of ⅓₀ seconds, the image processing circuit 32 performs the image development processing in ⅟₆₀ seconds after the RAW image data is inputted, and waits for inputting of next RAW image data in the following ⅟₆₀ seconds (what is called an idle state).

The endoscope image generated at the image processing circuit 32 is transmitted from the transmitter 36 to the access point 5. The transmitter 36 transmits, to the access point 5, without delay, the endoscope image inputted from the image processing circuit 32. Specifically, since the endoscope image is inputted from the image processing circuit 32 for ⅟₆₀ seconds and image inputting is waited for the following ⅟₆₀ seconds, the transmitter 36 performs transmission operation at processing timings such as transmission of an image of one frame for ⅟₆₀ seconds→wait for ⅟₆₀ seconds→transmission of an image of one frame for ⅟₆₀ seconds→ . . . as illustrated in "transmission (10)".

The access point 5 has such performance that the access point 5 can receive endoscope images of 60 frames in each second. Therefore, the access point 5 receives an endoscope image of one frame transmitted from the transmitter 36 for ⅟₆₀ seconds. The access point 5 transmits the received endoscope image to the display device 4. Note that, as in the case in which a plurality of access points are interposed between the endoscope 2 and the image processing server 3, an endoscope image transmitted from the image processing server 3 often reaches the display device 4 through a plurality of access points. Therefore, in the time charts illustrated in FIGS. 3 to 6 and 8 to 11, "reception (9)" indicates a timing of reception at an access point that receives an endoscope image from the image processing server 3, and "transmission (10)" indicates a timing of transmission at an access point that lastly transmits an endoscope image to the display device 4 through a plurality of access points. Accordingly, data delay occurs through a plurality of access points. In FIGS. 3 to 6 and 8 to 11, this delay time duration is, for example, ⅔₀ seconds.

The receiver 44 of the display device 4 receives the endoscope image from the access point 5. The receiver 44 receives the endoscope image of one frame transmitted from the access point 5 for ⅟₆₀ seconds. Specifically, the receiver 44 performs reception operation at processing timings such as reception of an image of one frame for ⅟₆₀ seconds→wait for ⅟₆₀ seconds→reception of an image of one frame for ⅟₆₀ seconds→ . . . . The received endoscope image is inputted to the display 41. The display 41 displays the image after a wait time (for example, ⅔₀ seconds) set in advance has elapsed since the endoscope image is inputted. Note that start timing of the processing is sometimes defined with, for example, the number of accumulated frames instead of the wait time. For example, it may be defined that the processing starts when data of two frames is accumulated in a buffer.

Since the processing performance of the display device 4 is 60 fps, the display 41 can display endoscope images of 60 frames in each second. However, since an endoscope image of one frame is inputted at intervals of ⅓₀ seconds, the display 41 displays an endoscope image of one frame for ⅟₆₀ seconds and displays the currently displayed frame for the following ⅟₆₀ seconds until a next endoscope image is inputted.

Through the above-described processing sequence, an image pickup signal (RAW image data) acquired at the image pickup device 22b is displayed as an endoscope image on the display device 4. Specifically, the delay time duration that is a time duration from image pickup to display is 26/60 seconds.

Figure 4:
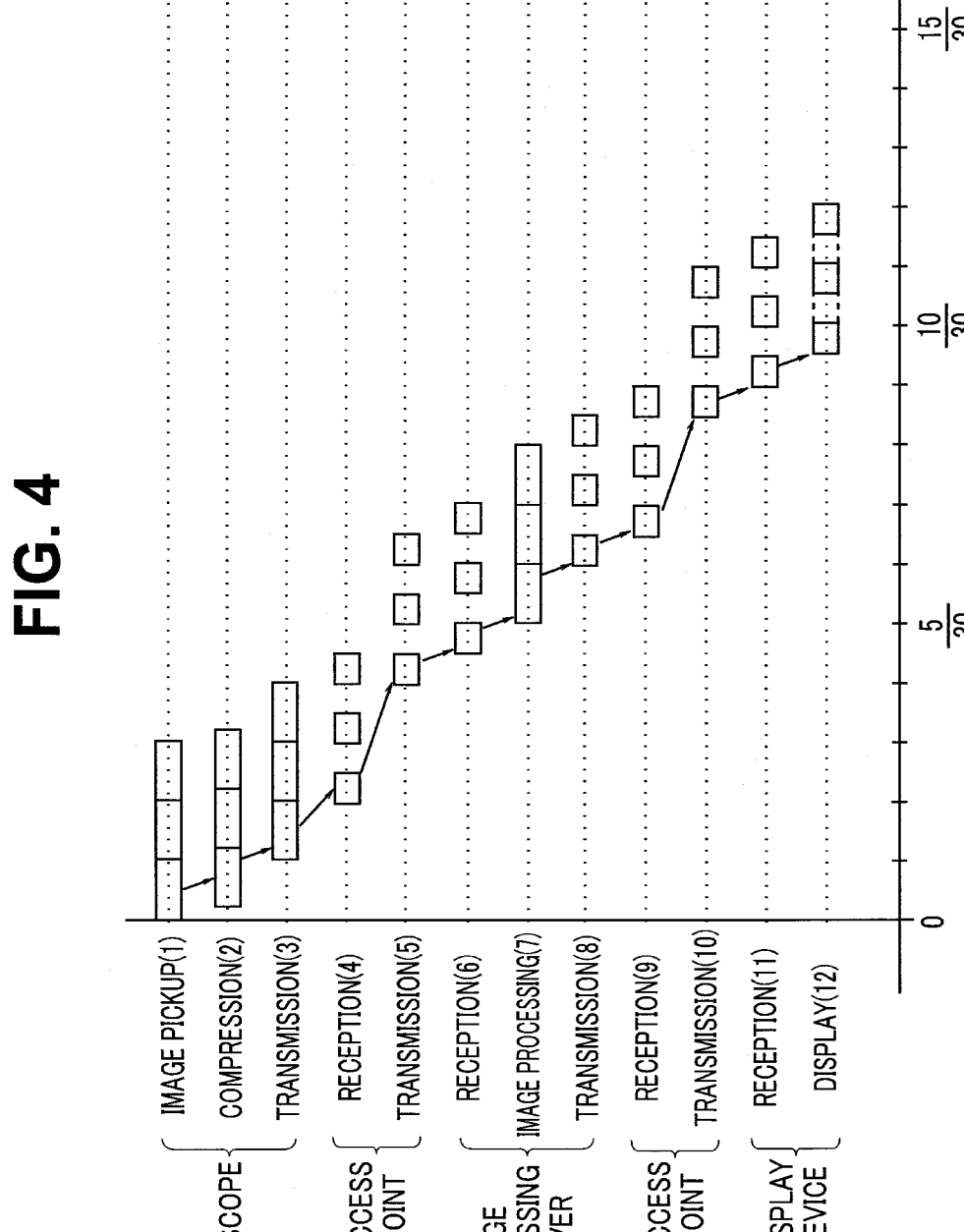
FIG. 4 is a time chart for description of a processing sequence related to an endoscope image.

<Processing Sequence of FIG. 4>

The optimized processing sequence illustrated in FIG. 4 will be described below. In the processing sequence illustrated in FIG. 4, processes ("image pickup (1)", "compression (2)", and "transmission (3)") at the endoscope 2 and processes ("reception (4)", "transmission (5)", "reception (9)", and "transmission (10)") at the access point 5 are performed at the processing timings illustrated in FIG. 3. Differences from FIG. 3 are processes at the image processing server 3 and processes at the display device 4.

Specifically, first, the wait time set between "reception (6)" and "image processing (7)" at the image processing server 3 is changed to set such processing timings that image development starts without delay after a RAW image of one frame is received. Accordingly, the delay time duration is shortened by 5/60 seconds as compared to the processing sequence of FIG. 3. Subsequently, the wait time set between "reception (11)" and "display (12)" at the display device 4 is changed to set such processing timings that display on the display 41 starts without delay after an endoscope image of one frame is received. Accordingly, the delay time duration is shortened by 3/60 seconds as compared to the processing sequence of FIG. 3.

Then, processing capability of the image processing circuit 32 is adjusted to an input timing of RAW image data. The processing capability is decreased from 60 fps to 30 fps by performing image processing by using the idle state until inputting of next RAW image data. Processing cost (for example, electric power consumption) of the image processing circuit 32 can be reduced by decreasing the processing capability.

Processing cost reduction in the time chart is illustrated as follows. A horizontal length of a rectangle representing a processing time duration of one frame in "image processing (7)" in FIG. 4 is twice as a horizontal length of a rectangle representing the processing time duration of one frame in "image processing (7)" in FIG. 3. Thus, processing capability of processing represented by a rectangle can be decreased by increasing a horizontal length of the rectangle, and accordingly, processing cost can be reduced.

Note that when the processing capability of the image processing circuit 32 is decreased to 30 fps, a timing of outputting an endoscope image from the image processing circuit 32 is delayed by 1/60 seconds.

Through the change of these three processing timings, the delay time duration that is a time duration from image pickup to display becomes 19/60 seconds, and thus the delay time duration is shortened by 7/60 seconds as compared to before the optimization. Moreover, the processing cost of the image processing circuit 32 can be reduced through appropriate adjustment of processing capability.

(2) Case in which Processing Cost of the Endoscope 2 and the Image Processing Server 3 is Reduced Processing sequence optimization in a case in which processing costs of the endoscope 2 and the image processing server 3 can be reduced will be described below.

In the medical system in FIG. 1, the image processing server 3 is connected to one endoscope 2. In addition, a configuration in which the image processing server 3 is connected to a plurality of endoscopes 2 and image pickup signals transmitted from the plurality of endoscopes 2 are provided with image processing at the one image processing server 3 may be achieved to efficiently use the image processing server 3. With this configuration, the image processing server 3 potentially receives data in an amount exceeding processing performance from the plurality of endoscopes 2. In such a case, processing sequence optimization is achieved by reducing the processing cost of the endoscope 2 to reduce the amount of signals transmitted to the image processing server 3 and by reducing the processing cost of the image processing server 3 not to receive data in an amount exceeding the processing performance.

Figure 5:
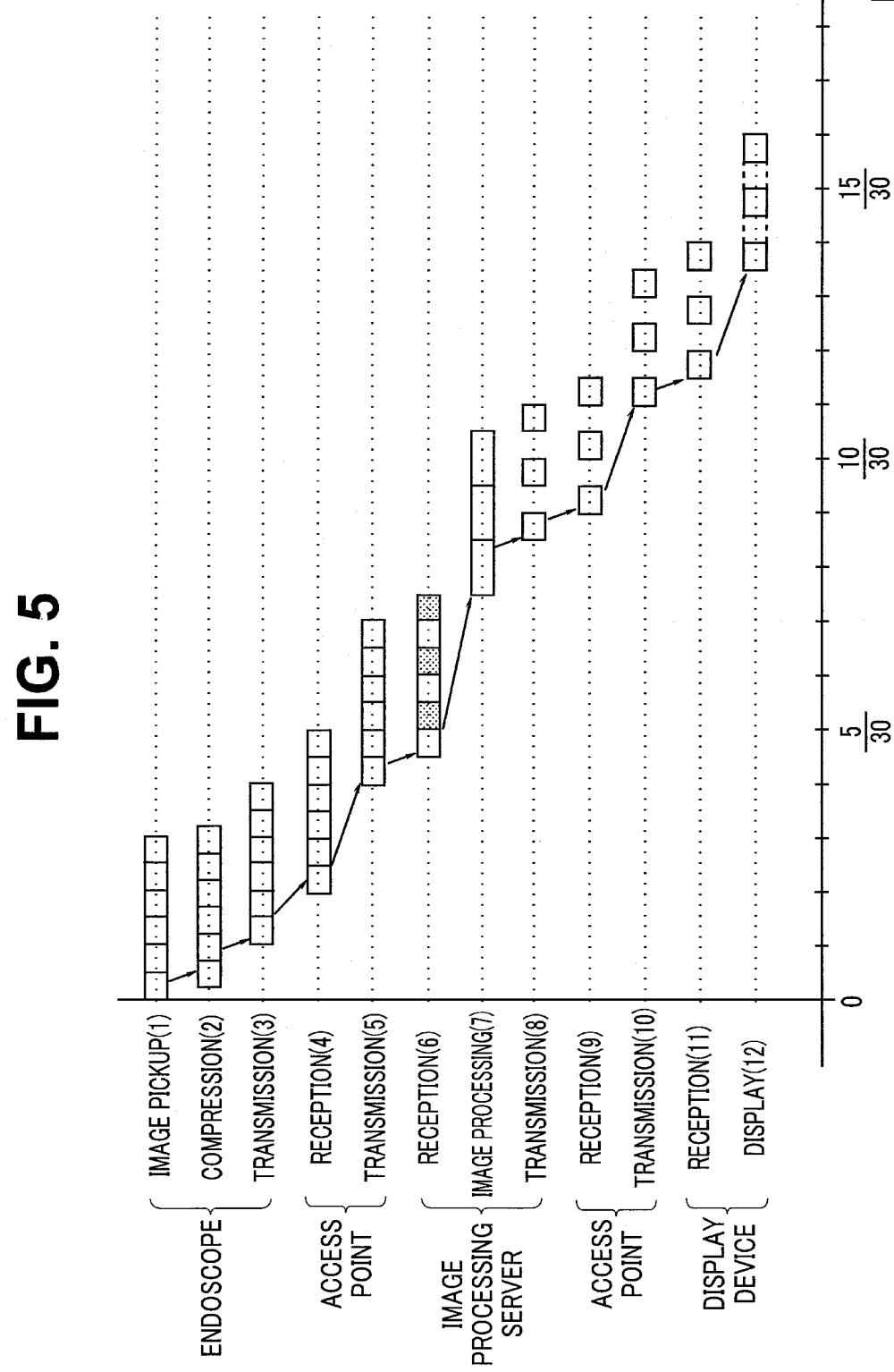
FIG. 5 is a time chart for description of a processing sequence related to an endoscope image.

With the configuration in which the image processing server 3 is connected to one endoscope 2, as well, processing sequence optimization is achieved in the same manner when the processing performance of the endoscope 2 is higher than the processing performance of the image processing server 3. A case in which the processing performance of the endoscope 2 and the display device 4 is 60 fps and the processing performance of the image processing server 3 is 30 fps will be described below with reference to FIGS. 5 and 6. FIG. 5 corresponds to an example of the processing sequence before optimization, and FIG. 6 corresponds to an example of a processing sequence obtained by optimizing the sequence illustrated in FIG. 5. Note that processing sequence optimization is performed mainly for processing cost reduction below. Thus, optimization methods below are applicable to a processing sequence for which delay is minimized. (However, similarly to the above-described case of (1), delay minimization is possible for a processing sequence for which delay is yet to be minimized.)

<Processing Sequence of FIG. 5>

The processing sequence illustrated in FIG. 5 will be described first. First, an image of the object is picked up at the image pickup device 22b of the endoscope 2. Since the processing performance of the endoscope 2 is 60 fps, the image pickup device 22b acquires image pickup signals of 60 frames in each second. In other words, the image pickup device 22b acquires an image pickup signal of one frame in 1/60 seconds. The acquired image pickup signal (RAW image data) is outputted from the image pickup device 22b to the data compressor 27 without delay.

The data compressor 27 compresses the inputted RAW image data at a predetermined compression ratio and then outputs the compressed data to the transmitter 29. The transmitter 29 wirelessly transmits the RAW image data inputted from the data compressor 27 to the access point 5. The transmitter 29 transmits RAW image data of one frame to the access point 5 in each 1/60 seconds.

The access point 5 has such performance that the access point 5 can receive RAW image data of 60 frames in each second. Therefore, the access point 5 receives the RAW image data of one frame transmitted from the transmitter 29 for 1/60 seconds. The access point 5 transmits the received RAW image data to the image processing server 3.

The receiver 35 of the image processing server 3 receives the RAW image data from the access point 5. The receiver 35 receives the RAW image data of one frame transmitted from the access point 5 for 1/60 seconds. The received RAW image data is inputted to the image processing circuit 32. The image processing circuit 32 starts image development processing after a wait time (for example, 3/30 seconds) set in advance has elapsed since the RAW image is inputted. The RAW image data is converted into an endoscope image through the image development processing. Since the processing performance of the image processing server 3 is 30 fps, the image processing circuit 32 can perform image development of RAW image data of 30 frames in each second. However, since RAW image data of one frame is inputted at intervals of 1/60 seconds, the image processing circuit 32 performs image development processing of RAW image data of the first frame in ⅓₀ seconds after the RAW image data of the frame is inputted, and performs image development processing of RAW image data of the third frame in the following ⅓₀ seconds. In other words, RAW image data of the second frame is not provided with image development processing due to mismatch between inputting speed and image development processing and is discarded. This is the same for the fourth frame, RAW image data of an odd-numbered frame is provided with image development processing, but RAW image data of an even-numbered frame cannot be provided with image development processing and is discarded. Note that, in FIG. 5, any frame that is received by the image processing server 3 in "reception (6)" but not provided with "image processing (7)" and is discarded is hatched.

The endoscope image generated at the image processing circuit 32 is transmitted from the transmitter 36 to the access point 5. The transmitter 36 transmits, to the access point 5, without delay, the endoscope image inputted from the image processing circuit 32. Specifically, as illustrated in "transmission (10)", the transmitter 36 performs transmission operation at processing timings such as transmission of an image of one frame for ¹⁄₆₀ seconds→wait for ¹⁄₆₀ seconds→transmission of an image of one frame for ¹⁄₆₀ seconds→ . . . .

The access point 5 has such performance that the access point 5 can receive endoscope images of 60 frames in each second. Therefore, the access point 5 receives the endoscope image of one frame transmitted from the transmitter 36 for ¹⁄₆₀ seconds. The access point 5 transmits the received endoscope image to the display device 4.

The receiver 44 of the display device 4 receives the endoscope image from the access point 5. The receiver 44 receives the endoscope image of one frame transmitted from the access point 5 for ¹⁄₆₀ seconds. Specifically, the receiver 44 performs reception operation at processing timings such as reception of an image of one frame for ¹⁄₆₀ seconds→wait for ¹⁄₆₀ seconds→reception of an image of one frame for ¹⁄₆₀ seconds→ . . . . The received endoscope image is inputted to the display 41. The display 41 displays the image after a wait time (for example, ²⁄₃₀ seconds) set in advance has elapsed since the endoscope image is inputted. Since the processing performance of the display device 4 is 60 fps, the display 41 can display endoscope images of 60 frames in each second. However, since an endoscope image of one frame is inputted at intervals of ⅓₀ seconds, the display 41 displays an endoscope image of one frame for ¹⁄₆₀ seconds and repeatedly displays the currently displayed frame in the following ¹⁄₆₀ seconds until a next endoscope image is inputted.

Through the above-described processing sequence, an image pickup signal (RAW image data) acquired at the image pickup device 22b is displayed as an endoscope image on the display device 4. Specifically, the delay time duration that is a time duration from image pickup to display is 27/60 seconds. Half of image pickup signals acquired at the image pickup device 22b cannot be provided with image processing but are discarded.

Figure 6:
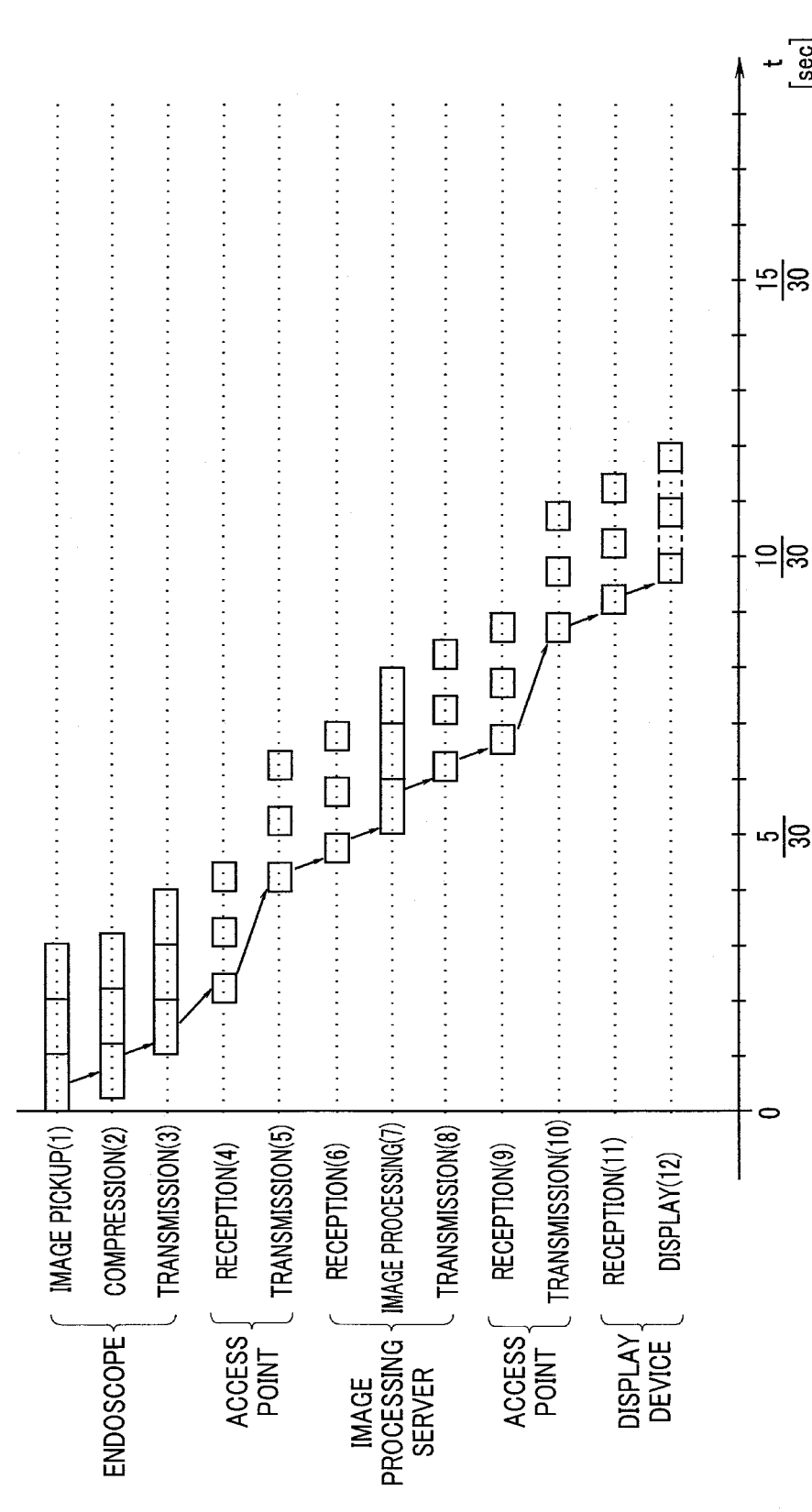
FIG. 6 is a time chart for description of a processing sequence related to an endoscope image.

<Processing Sequence of FIG. 6>

The optimized processing sequence illustrated in FIG. 6 will be described below. In the processing sequence illustrated in FIG. 6, processes ("reception (4)", "transmission (5)", "reception (9)", and "transmission (10)") at the access point 5 are performed at the timings illustrated in FIG. 5. Differences from FIG. 5 are processes at the endoscope 2, processes at the image processing server 3, and processes at the display device 4.

Specifically, first, the wait time set between "reception (6)" and "image processing (7)" at the image processing server 3 is changed to set such processing timings that image development starts without delay after a RAW image of one frame is received. Accordingly, the delay time duration is shortened by ⁵⁄₆₀ seconds as compared to the processing sequence of FIG. 5. Subsequently, the wait time set between "reception (11)" and "display (12)" at the display device 4 is changed to set such processing timings that display on the display 41 starts without delay after an endoscope image of one frame is received. Accordingly, the delay time duration is shortened by ³⁄₆₀ seconds as compared to the processing sequence of FIG. 3.

Then, processing capability of the endoscope 2 is adjusted to capability of image development processing of RAW image data at the image processing server 3. Specifically, the processing capability of the endoscope 2 is decreased from 60 fps to 30 fps. When the processing capability is decreased, RAW image data obtained by image pickup at the image pickup device 22b and transmitted to the image processing server 3 is all developed at the image processing circuit 32. In other words, the processing cost of the endoscope 2 is reduced by not acquiring unnecessary data that cannot be processed at the image processing server 3.

Processing cost reduction in the time chart is illustrated as follows. A horizontal length of a rectangle representing the processing time duration of one frame in each of the lanes of "image pickup (1)", "compression (2)", and "transmission (3)" in FIG. 6 is twice as a horizontal length of a rectangle representing the processing time duration of one frame in a corresponding lane in FIG. 5. Thus, processing capability of processing represented by a rectangle can be decreased by increasing a horizontal length of the rectangle, and accordingly, processing cost can be reduced. The number of rectangles illustrated in the lane of "reception (6)" in FIG. 6 is half the number of rectangles illustrated in the lane of "reception (6)" in FIG. 5. Thus, processing cost of one lane can be reduced by reducing the number of rectangles illustrated in the lane.

Through the change of these three processing timings, the delay time duration that is a time duration from image pickup to display becomes 19/60 seconds, and thus the delay time duration is shortened by ⁸⁄₆₀ seconds as compared to before the optimization. Moreover, the processing cost of the endoscope 2 can be reduced through appropriate adjustment of processing capability. Furthermore, electric power consumption can be reduced by reducing the processing cost of the endoscope 2. Through the reduction of electric power consumption, a drive time can be extended when the endoscope 2 is driven by a battery such as a battery cell.

(3) Case in which Network Communication Performance is Low

Processing sequence optimization in a case in which network communication performance is low will be described below. Examples of cases in which the network communication performance is low include a case in which performance of the access point 5 is low and a case in which a large number of wireless instruments are connected to the access point 5 and communication quality of the access point 5 degrades.

Figure 7:
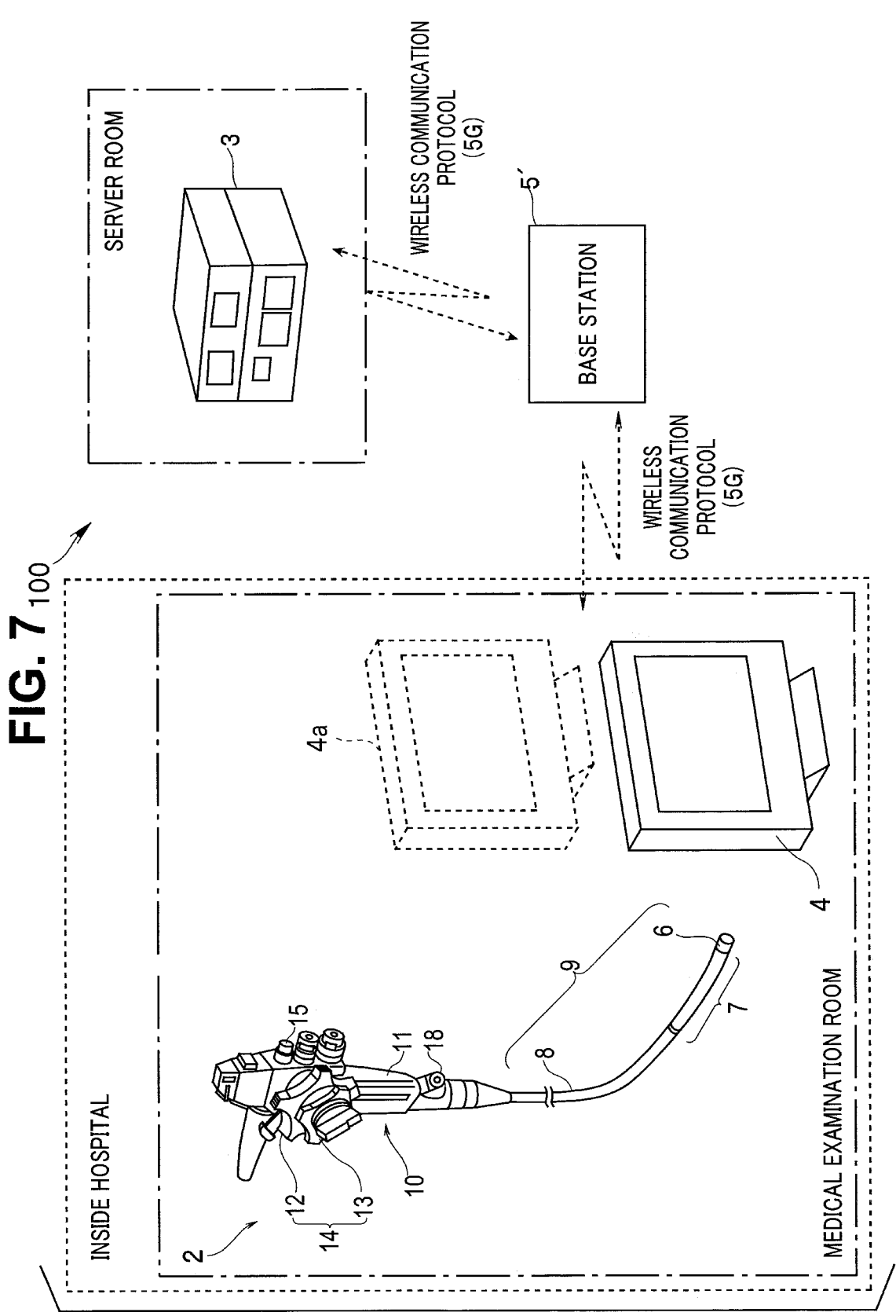
FIG. 7 is a diagram for description of another example of the entire configuration of the medical system according to the embodiment of the present invention.

<Processing Sequence of FIG. 7>

FIG. 7 is a diagram for description of another example of the entire configuration of the medical system according to the embodiment of the present invention. The network communication performance degrades in some cases with a configuration in which the image processing server 3 is installed outside the hospital and communicates with the endoscope 2 and the display device 4 installed inside the hospital through a base station 5' as a relay device as illustrated in FIG. 7. An entire network in the medical system may be unified to a communication scheme compliant with 5G as a mobile communication standard, or a local network (in-hospital LAN) may be established in the hospital by using, for example, a communication scheme compliant with Local 5G, the in-hospital LAN and the base station 5' may be connected through a network, and the base station 5' and the image processing server 3 may be connected through another network. When communication is performed through connection of locally established networks in this manner, communication performance potentially degrades due to network complexity.

Figure 8:
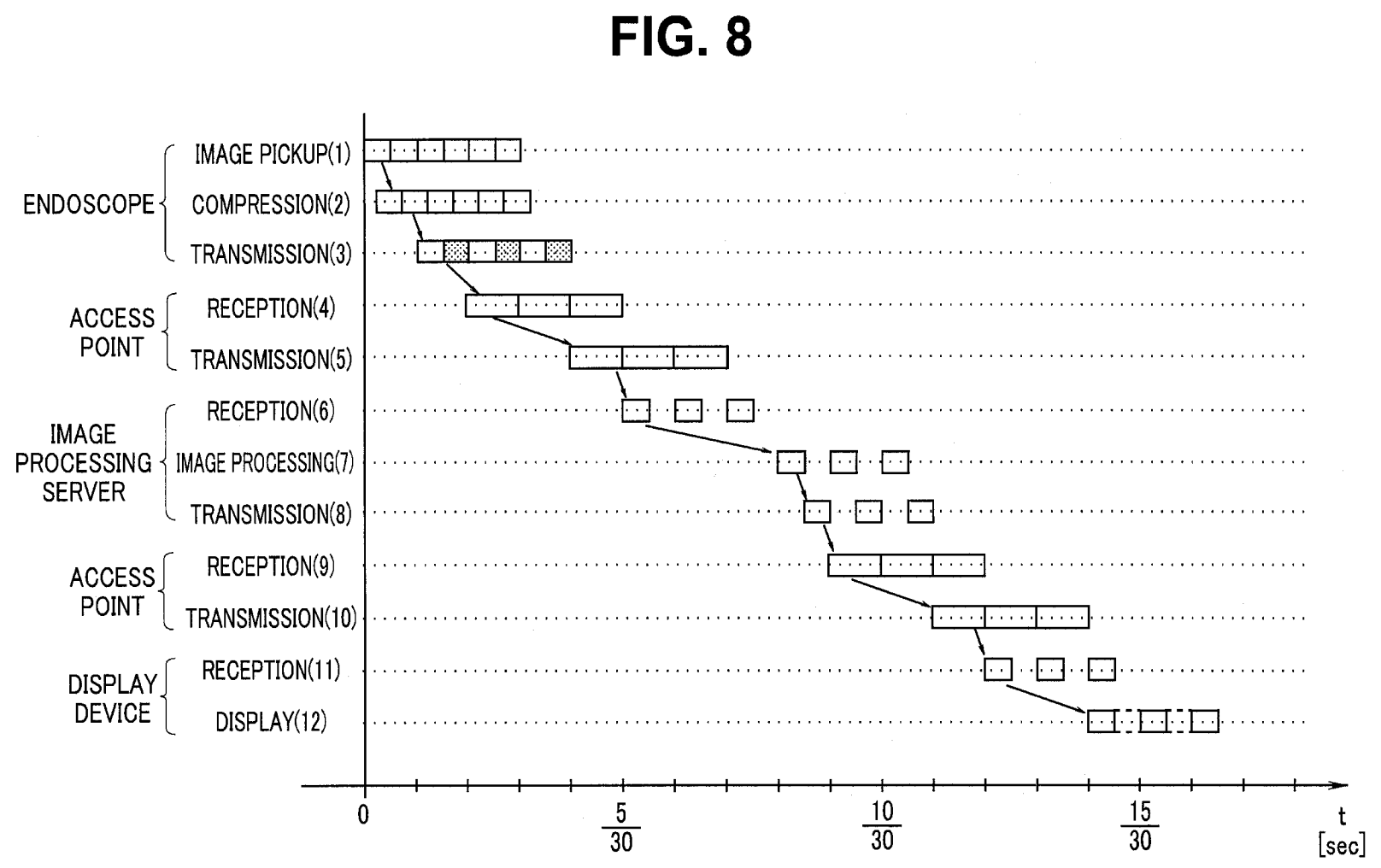

A case in which the performance of the access point 5 is low (the processing performance of the endoscope 2, the image processing server 3, and the display device 4 is 60 fps, and the access point 5 has performance that the access point 5 can receive RAW image data of 30 frames for each second) will be described below. FIG. 8 corresponds to an example of the processing sequence before optimization, and FIG. 9 corresponds to an example of a processing sequence obtained by optimizing the sequence illustrated in FIG. 8.

<Processing Sequence of FIG. 8>

The processing sequence illustrated in FIG. 8 will be described first. An image of the object is picked up at the image pickup device 22b of the endoscope 2. Since the processing performance of the endoscope 2 is 60 fps, the image pickup device 22b acquires image pickup signals of 60 frames in each second. In other words, the image pickup device 22b acquires an image pickup signal of one frame in $\frac{1}{60}$ seconds. The acquired image pickup signal (RAW image data) is outputted from the image pickup device 22b to the data compressor 27 without delay.

The data compressor 27 compresses the inputted RAW image data at a predetermined compression ratio and then outputs the compressed data to the transmitter 29. The transmitter 29 wirelessly transmits the RAW image data inputted from the data compressor 27 to the access point 5. The transmitter 29 transmits RAW image data of one frame to the access point 5 in each $\frac{1}{60}$ seconds.

The access point 5 has performance that the access point 5 can receive RAW image data of 30 frames in each second. Therefore, the access point 5 receives RAW image data of one frame transmitted from the transmitter 29 for $\frac{1}{30}$ seconds. However, RAW image data of one frame is inputted from the endoscope 2 at intervals of $\frac{1}{60}$ seconds. In other words, RAW image data of two frames is transmitted from the endoscope 2 while the access point 5 receives RAW image data of one frame. Due to this mismatch, the access point 5 can receive only half of transmitted RAW image data. For example, RAW image data of odd-numbered frames such as the first frame, the third frame, . . . can be received, but RAW image data of even-numbered frames such as the second frame, the fourth frame, . . . cannot be received but is discarded. The access point 5 transmits received RAW image data to the image processing server 3 at speed of $\frac{1}{30}$ seconds per frame. Note that, in FIG. 8, any frame that is transmitted from the endoscope 2 in "transmission (3)" but not subjected to "reception (4)" at the access point and is discarded is hatched.

The receiver 35 of the image processing server 3 receives the RAW image data from the access point 5. The receiver 35 receives the RAW image data of one frame transmitted from the access point 5 for $\frac{1}{60}$ seconds. The received RAW image data is inputted to the image processing circuit 32. The image processing circuit 32 starts image development processing after a wait time (for example, $\frac{3}{30}$ seconds) set in advance has elapsed since the RAW image is inputted. The RAW image data is converted into an endoscope image through the image development processing. Since the processing performance of the image processing server 3 is 60 fps, the image processing circuit 32 can perform image development of RAW image data of 60 frames in each second. However, since RAW image data of one frame is inputted at intervals of $\frac{1}{30}$ seconds, the image processing circuit 32 performs the image development processing in $\frac{1}{60}$ seconds after the RAW image data is inputted, and waits for inputting of next RAW image data in the following $\frac{1}{60}$ seconds (what is called an idle state).

The endoscope image generated at the image processing circuit 32 is transmitted from the transmitter 36 to the access point 5. The transmitter 36 transmits, to the access point 5, without delay, the endoscope image inputted from the image processing circuit 32. Specifically, since the endoscope image is inputted from the image processing circuit 32 for $\frac{1}{60}$ seconds and image inputting is waited for the following $\frac{1}{60}$ seconds, the transmitter 36 performs transmission operation at processing timings such as transmission of an image of one frame for $\frac{1}{60}$ seconds→wait for $\frac{1}{60}$ seconds→transmission of an image of one frame for $\frac{1}{60}$ seconds→ . . . as illustrated in "transmission (10)".

The access point 5 has performance that the access point 5 can receive endoscope images of 30 frames in each second. Therefore, the access point 5 receives an endoscope image of one frame transmitted from the transmitter 36 for $\frac{1}{30}$ seconds. The access point 5 transmits the received endoscope image to the display device 4.

The receiver 44 of the display device 4 receives the endoscope image from the access point 5. The receiver 44 receives the endoscope image of one frame transmitted from the access point 5 for $\frac{1}{60}$ seconds. Specifically, the receiver 44 performs reception operation at processing timings such as reception of an image of one frame for $\frac{1}{60}$ seconds→wait for $\frac{1}{60}$ seconds→reception of an image of one frame for $\frac{1}{60}$ seconds→ . . . . The received endoscope image is inputted to the display 41. The display 41 displays the image after a wait time (for example, $\frac{2}{30}$ seconds) set in advance has elapsed since the endoscope image is inputted. Since the processing performance of the display device 4 is 60 fps, the display 41 can display endoscope images of 60 frames in each second. However, since an endoscope image of one frame is inputted at intervals of $\frac{1}{30}$ seconds, the display 41 displays an endoscope image of one frame for $\frac{1}{60}$ seconds and repeatedly displays the currently displayed frame in the following $\frac{1}{60}$ seconds until a next endoscope image is inputted.

Through the above-described processing sequence, an image pickup signal (RAW image data) acquired at the image pickup device 22b is displayed as an endoscope image on the display device 4. Specifically, the delay time duration that is a time duration from image pickup to display is 28/60 seconds. Half of image pickup signals acquired at the image pickup device 22b cannot be provided with image processing but are discarded.

Figure 9:
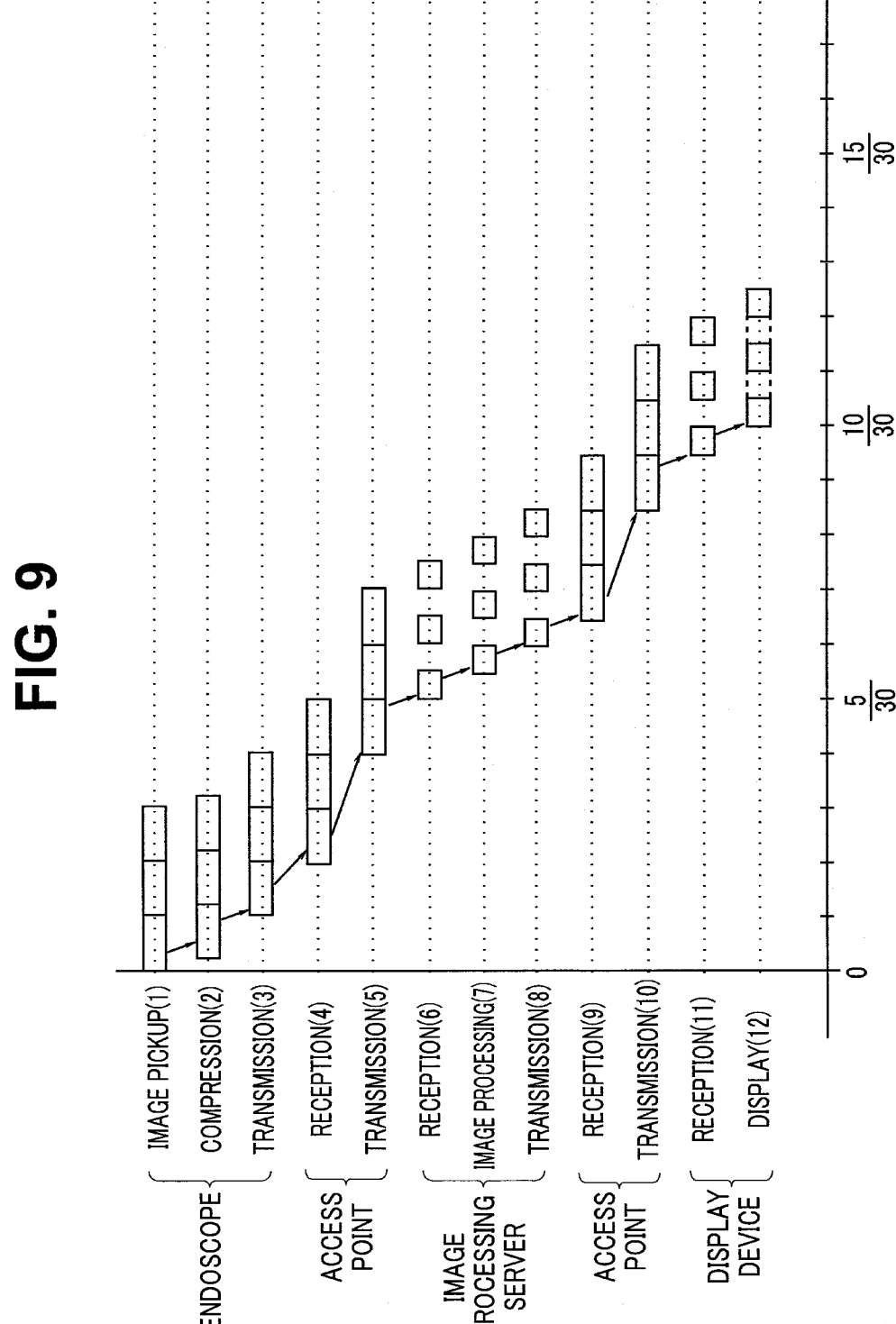
FIG. 9 is a time chart for description of a processing sequence related to an endoscope image.

<Processing Sequence of FIG. 9>

The optimized processing sequence illustrated in FIG. 9 will be described below. In the processing sequence illustrated in FIG. 9, processes ("reception (4)", "transmission (5)", "reception (9)", and "transmission (10)") at the access point 5 are performed at the processing timings illustrated in FIG. 8. Differences of FIG. 9 from FIG. 8 are processes at the endoscope 2, processes at the image processing server 3, and processes at the display device 4.

Specifically, first, the wait time set between "reception (6)" and "image processing (7)" at the image processing server 3 is changed to set such processing timings that image development starts without delay after a RAW image of one frame is received. Accordingly, the delay time duration is shortened by 5/60 seconds as compared to the processing sequence of FIG. 5. Subsequently, the wait time set between "reception (11)" and "display (12)" at the display device 4 is changed to set such processing timings that display on the display 41 starts without delay after an endoscope image of one frame is received. Accordingly, the delay time duration is shortened by 3/60 seconds as compared to the processing sequence of FIG. 3.

Then, the processing capability of the endoscope 2 is adjusted to communication performance of RAW image data at the access point 5. Specifically, the processing capability of the endoscope 2 is decreased from 60 fps to 30 fps. When the processing capability is decreased, RAW image data obtained by image pickup at the image pickup device 22b and transmitted to the access point 5 is all transmitted to the image processing circuit 32. In other words, the processing cost of the endoscope 2 is reduced by not acquiring, at the image pickup device 22b, unnecessary data that cannot be received at the access point 5.

Through the change of these three processing timings, the delay time duration that is a time duration from image pickup to display becomes 20/60 seconds, and thus the delay time duration is shortened by 8/60 seconds as compared to before the optimization. Moreover, the processing cost of the endoscope 2 can be reduced through appropriate adjustment of processing capability.

(4) Case in which the Processing Performance of the Display Device 4 is Low

Figure 10:
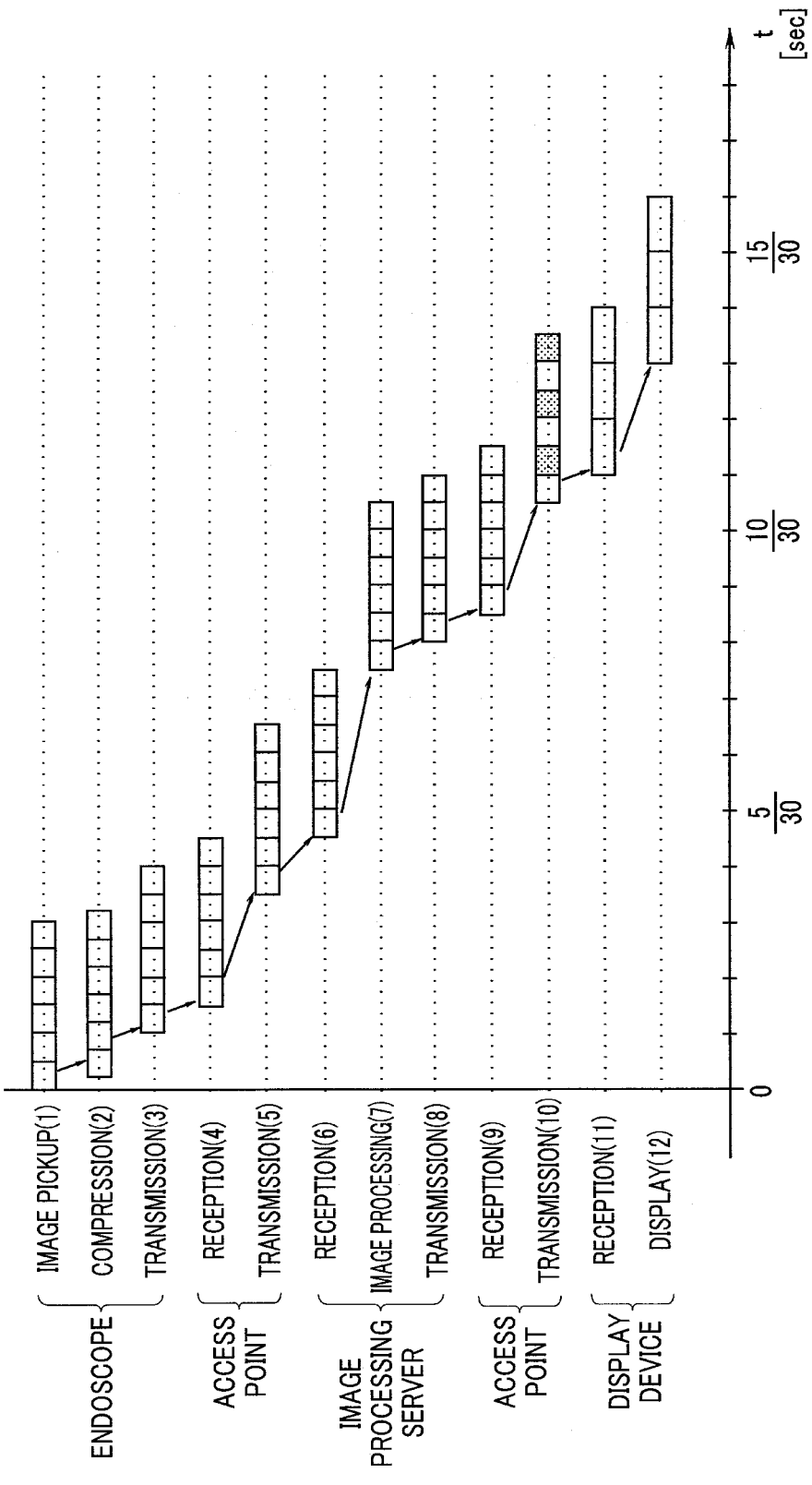
FIG. 10 is a time chart for description of a processing sequence related to an endoscope image.

Processing sequence optimization in a case in which the processing performance of the display device 4 is low will be described below with reference to FIGS. 10 and 11. A case in which the processing performance of the endoscope 2 and the image processing server 3 is 60 fps and the processing performance of the display device 4 is 30 fps will be described below. FIG. 10 corresponds to an example of the processing sequence before optimization, and FIG. 11 corresponds to an example of a processing sequence obtained by optimizing the sequence illustrated in FIG. 10.

<Processing Sequence of FIG. 10>

The processing sequence illustrated in FIG. 10 will be described first. First, an image of the object is picked up at the image pickup device 22b of the endoscope 2. Since the processing performance of the endoscope 2 is 60 fps, the image pickup device 22b acquires image pickup signals of 60 frames in each second. In other words, the image pickup device 22b acquires an image pickup signal of one frame in 1/60 seconds. The acquired image pickup signal (RAW image data) is outputted from the image pickup device 22b to the data compressor 27 without delay.

The data compressor 27 compresses the inputted RAW image data at a predetermined compression ratio and then outputs the compressed data to the transmitter 29. The transmitter 29 wirelessly transmits the RAW image data inputted from the data compressor 27 to the access point 5. The transmitter 29 transmits RAW image data of one frame to the access point 5 in each 1/60 seconds.

The access point 5 has such performance that the access point 5 can receive RAW image data of 60 frames in each second. Therefore, the access point 5 receives the RAW image data of one frame transmitted from the transmitter 29 for 1/60 seconds. The access point 5 transmits the received RAW image data to the image processing server 3.

The receiver 35 of the image processing server 3 receives the RAW image data from the access point 5. The receiver 35 receives the RAW image data of one frame transmitted from the access point 5 for 1/60 seconds. The received RAW image data is inputted to the image processing circuit 32. The image processing circuit 32 starts image development processing after a wait time (for example, 3/30 seconds) set in advance has elapsed since the RAW image is inputted. The RAW image data is converted into an endoscope image through the image development processing. Since the processing performance of the image processing server 3 is 60 fps, the image processing circuit 32 can perform image development of RAW image data of 60 frames in each second. The endoscope image generated at the image processing circuit 32 is transmitted from the transmitter 36 to the access point 5. The transmitter 36 transmits, to the access point 5, without delay, the endoscope image inputted from the image processing circuit 32.

The access point 5 has such performance that the access point 5 can receive endoscope images of 60 frames in each second. Therefore, the access point 5 receives the endoscope image of one frame transmitted from the transmitter 36 for 1/60 seconds. The access point 5 transmits the received endoscope image to the display device 4.

The receiver 44 of the display device 4 receives the endoscope image from the access point 5. The receiver 44 receives the endoscope image of one frame transmitted from the access point 5 for 1/30 seconds. However, an endoscope image of one frame is transmitted from the access point 5 to the display device 4 at intervals of 1/60 seconds. In other words, endoscope images of two frames are transmitted from the access point 5 while the display device 4 receives an endoscope image of one frame. Due to this mismatch, the display device 4 can receive only half of transmitted endoscope images. For example, endoscope images of odd-numbered frames such as the first frame, the third frame, . . . can be received, but endoscope images of even-numbered frames such as the second frame, the fourth frame, . . . cannot be received but are discarded. Thus, only the endoscope images of the odd-numbered frames are displayed on the display 41. Note that, in FIG. 10, any frame that is transmitted from the access point 5 in "transmission (10)" but not subjected to "reception (11)" at the display device 4 and is discarded is hatched.

Through the above-described processing sequence, an image pickup signal (RAW image data) acquired at the image pickup device 22b is displayed as an endoscope image on the display device 4. Specifically, the delay time duration that is a time duration from image pickup to display is 26/60 seconds. Half of image pickup signals acquired at the image pickup device 22b are not received at the display device 4 but are discarded.

Figure 11:
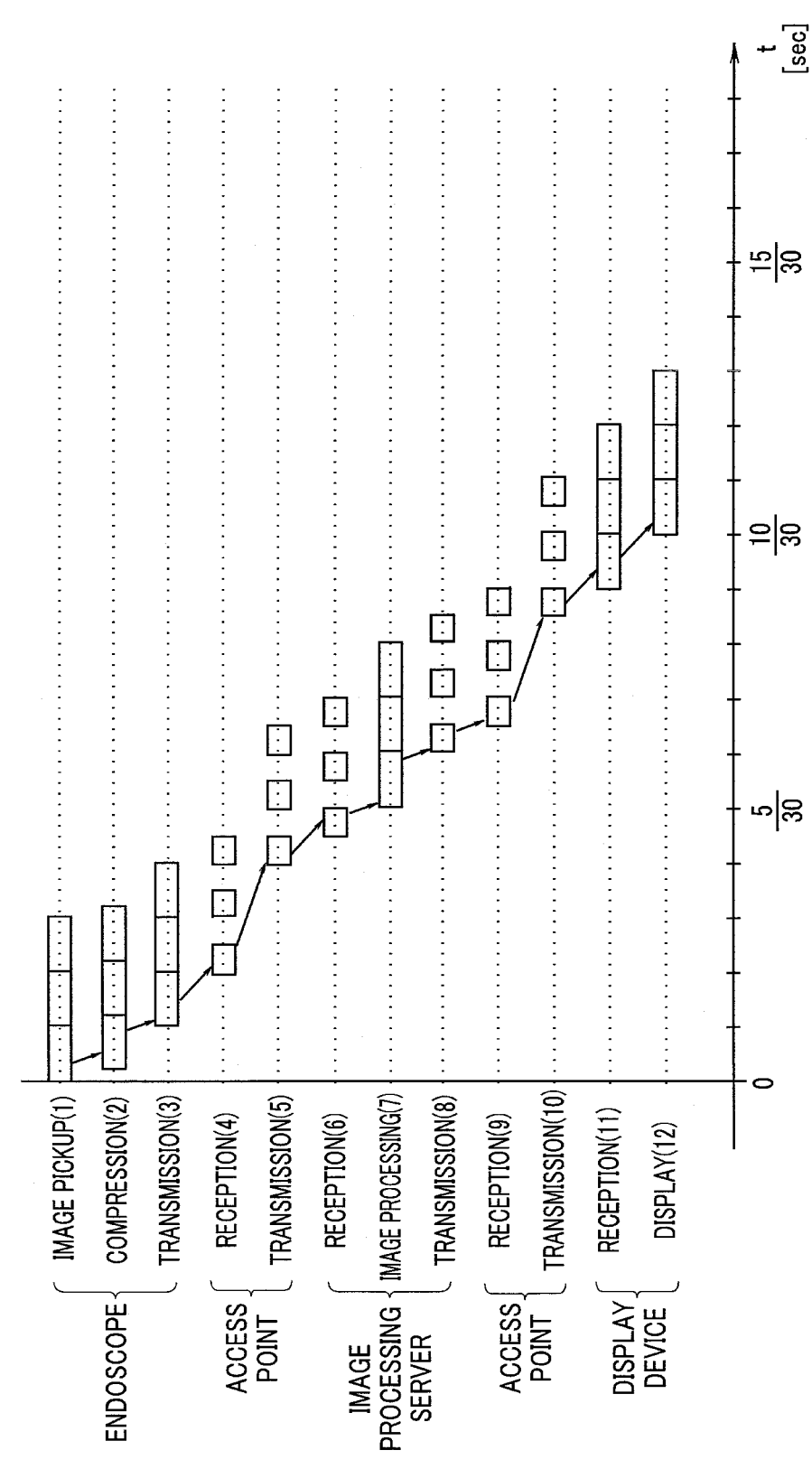
FIG. 11 is a time chart for description of a processing sequence related to an endoscope image.

<Processing Sequence of FIG. 11>

The optimized processing sequence illustrated in FIG. 11 will be described below. In the processing sequence illustrated in FIG. 11, processes ("reception (4)", "transmission (5)", "reception (9)", and "transmission (10)") at the access point 5 are performed at the processing timings illustrated in FIG. 10. Differences from FIG. 10 are processes at the endoscope 2, processes at the image processing server 3, and processes at the display device 4.

Specifically, first, the wait time set between "reception (6)" and "image processing (7)" at the image processing server 3 is changed to set such processing timings that image development starts without delay after a RAW image of one frame is received. Accordingly, the delay time duration is shortened by 5/60 seconds as compared to the processing sequence of FIG. 5. Subsequently, the wait time set between "reception (11)" and "display (12)" at the display device 4 is changed to set such processing timings that display on the display 41 starts without delay after an endoscope image of one frame is received. Accordingly, the delay time duration is shortened by ⅔₀ seconds as compared to the processing sequence of FIG. 10.

Then, the processing capability of the endoscope 2 is adjusted to capability of image development processing of RAW image data at the image processing server 3. Specifically, the processing capability of the endoscope 2 is decreased from 60 fps to 30 fps. In addition, the processing capability of the image processing circuit 32 at the image processing server 3 is decreased from 60 fps to 30 fps. When the processing capabilities are decreased, RAW image data obtained by image pickup at the image pickup device 22b is all developed at the image processing circuit 32, and all image development data (endoscope images) is displayed on the display device 4. In other words, the processing costs of the endoscope 2 and the image processing server 3 is reduced by not acquiring unnecessary data that cannot be processed at the display device 4. Note that when the processing capability of the image processing circuit 32 is decreased to 30 fps, a timing of outputting an endoscope image from the image processing circuit 32 is delayed by ⅟₆₀ seconds.

Through the change of these three processing timings, the delay time duration that is a time duration from image pickup to display becomes 20/60 seconds, and thus the delay time duration is shortened by ⅞₀ seconds as compared to before the optimization. Moreover, the processing cost of the endoscope 2 and the processing cost of the image processing server 3 can be reduced through appropriate adjustment of processing capability.

As described above, the communication control circuit 33 specifies the endoscope 2 as a transmission source of RAW image data, the display device 4 as a transmission destination of an endoscope image after image development, and a relay device (for example, the access point 5) on a communication path. Then, the communication control circuit 33 optimizes a processing sequence based on the first processing specification of the endoscope 2, the second processing specification of the image processing server 3, the third processing specification of the display device 4, and a communication specification of the relay device. Then, the communication control circuit 33 transmits processing specifications based on the optimized processing sequence to the endoscope 2 and the display device 4. The communication control circuit 33 transmits a fourth processing specification thus optimized to the endoscope 2 and a fifth processing specification thus optimized to the display device 4.

The endoscope 2 and the display device 4 each execute a processing sequence based on the corresponding processing specification received from the communication control circuit 33. The image processing server 3 executes a processing sequence based on a processing specification optimized at the communication control circuit 33. Accordingly, costs of processing and communication can be reduced and the processing time duration from image pickup to display can be shortened to improve a real-time property.

Note that although the examples in which processing optimization is performed in units of frames are described above with reference to FIGS. 3 to 6 and 8 to 11, each frame may be divided into a plurality of subframes and processing and communication may be performed in units of subframes. Hereinafter, processing in units of frames is referred to as processing in a first processing unit, and processing in units of subframes is referred to as processing in a second processing unit.

All or part of processing at the communication control circuit 33 may be performed by a software program. Specifically, the non-illustrated processor provided in the signal processing circuit 31 may perform, for example, the same processing and operation as the communication control circuit 33 by executing a computer program read from the storage device 34.

<Flowchart>

Figure 12:
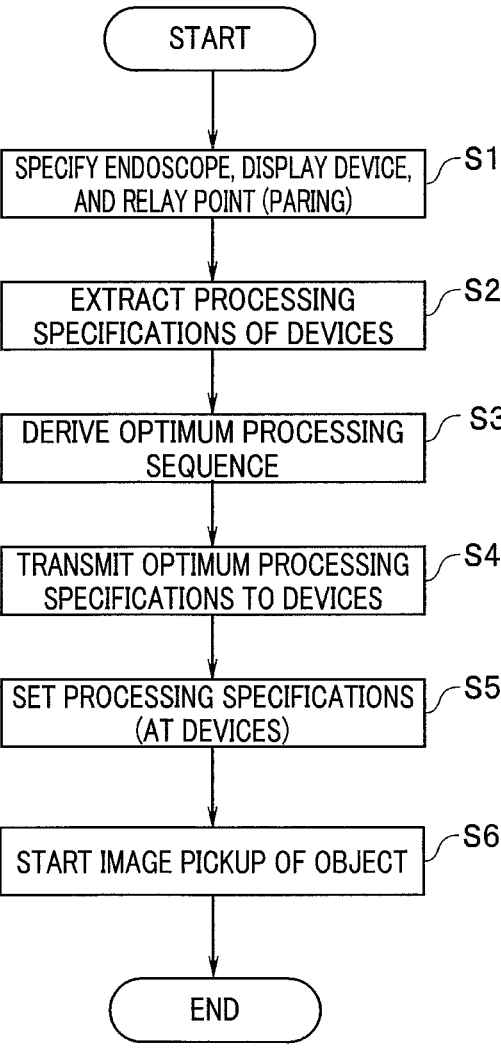
FIG. 12 is a flowchart illustrating effects of the present embodiment.

FIG. 12 is a flowchart illustrating effects of the present embodiment. The flowchart illustrated in FIG. 12 is a diagram for description of a procedure of optimizing a series of processes from object image pickup to endoscope image display in the medical system 100.

(S1)

First, the image processing server 3 performs pairing between the endoscope 2 that picks up an image of an object and transmits RAW image data and the display device 4 that displays an endoscope image developed at the image processing server 3. In addition, the image processing server 3 specifies a relay point (such as the access point 5) between the endoscope 2 and the image processing server 3 and a relay device between the image processing server 3 and the display device 4.

(S2)

Subsequently, the image processing server 3 extracts from the storage device 34 the processing specifications of the endoscope 2 and the display device 4 paired at S1. Each processing specification includes processing speed (frame rate), a processing unit (frame/subframe), and a processing start timing (a time lag from data reception to processing start or a processing start condition). The image processing server 3 also acquires the communication protocol (such as communication speed) of the relay device.

(S3)

Subsequently, the communication control circuit 42 derives an optimum processing sequence based on the processing specifications and the communication protocol extracted at S2.

(S4)

The image processing server 3 transmits processing specification data to the endoscope 2 and the display device 4 based on the processing sequence derived at S3, thereby providing instructions of the processing specifications.

(S5)

The endoscope 2 and the display device 4 set and change the processing specifications as necessary based on the received processing specification data. For example, the endoscope 2 sets and changes a frame rate of the image pickup device 22b and a transmission rate of RAW image data. The image processing server 3 sets and changes the processing specification as necessary.

(S6)

Image pickup of the object starts at the endoscope 2 in accordance with the processing specification set at S5. RAW image data obtained by the image pickup is transmitted to and developed at the image processing server 3 and displayed as an endoscope image on the display device 4.

According to the present embodiment, it is possible to reduce costs of processing and communication and shorten the processing time duration from image pickup to display, thereby providing a medical system having an improved real-time property.

Note that the medical system 100 of the present embodiment is not limited to a system established in a hospital, but for example, the image processing server 3 may be installed outside the hospital. Such a configuration is effective for a case in which RAW image data transmitted from endoscopes 2 in a plurality of hospitals is concentratively processed at one image processing server 3 through Internet connection or the like. Alternatively, the display device 4 may be installed outside a hospital and an endoscope image picked up by an examiner in the hospital may be displayed on the display device 4 outside the hospital through Internet connection or the like. Such a configuration is best suited for a remote diagnosis. Thus, installation places are not particularly limited as long as the endoscope 2, the image processing server 3, and the display device 4 are in environments where they can transmit and receive data to and from each other through a wireless/wired network. Moreover, the endoscope 2 and the display device 4 may be connected through a wired cable and communication between the endoscope 2 and the image processing server 3 may be performed through the display device 4. With this configuration, it is possible to simplify a configuration of a site related to a communication interface of the endoscope 2, thereby reducing cost.

The medical system 100 of the present embodiment may perform two or more of the processing sequence optimization methods described above in (1) to (4) in combination instead of performing each of the methods alone.

The image processing server 3 may have not only a function to develop an endoscope image but also a secondary service function such as a function to perform an automatic diagnosis using the developed endoscope image. In such a case, the communication control circuit 33 preferably derives an optimum processing sequence with processing speed of the secondary service function taken into consideration as well.

The embodiment of the present invention is described above but the embodiment is merely exemplary and not intended to limit the scope of the invention. This novel embodiment may be performed in other various forms and provided with various kinds of omission, replacement, and change without departing from the gist of the invention. The embodiment and any modification are included in the scope and gist of the invention and also included in the invention written in the claims and equivalents of the invention.

What is claimed is:

1. A medical system comprising:
an image pickup instrument configured to output an image pickup signal acquired by picking up an image of an object;
a signal processing device configured to generate an observation image from the image pickup signal;
at least one display device configured to display the observation image; and
a relay device configured to connect the image pickup instrument, the signal processing device, and the display device,
wherein the signal processing device derives a processing sequence that minimizes a time duration from when the image pickup instrument picks up an image of an object until the display device displays the observation image, based on a first processing specification of the image pickup signal at the image pickup instrument, a second processing specification of the signal processing device, a third processing specification of the observation image at the display device, and a communication protocol of the relay device, provides instruction of a fourth processing specification to the image pickup instrument based on the processing sequence, and provides instruction of a fifth processing specification to the display device based on the processing sequence.

2. The medical system according to claim 1, wherein
the first processing specification is a first frame rate at which the image pickup signal is acquired and a first transmission unit in which the image pickup signal is transmitted,
the second processing specification is a second frame rate in image development processing of generating the observation image from the image pickup signal and a start condition of the image development processing, and
the third processing specification is a third frame rate in display processing of displaying the observation image and a start condition of the display processing.

3. The medical system according to claim 1, wherein the image pickup instrument, the relay device, the signal processing device, and the display device transmit and receive data through Internet connection.

4. The medical system according to claim 1, wherein
the image pickup instrument further includes at least one of a light modulator configured to modulate irradiation light with which an object is irradiated, a gas/liquid feeder configured to perform gas/liquid feeding, an energy treatment device configured to perform energy treatment, or a control circuit configured to control the light modulator, the gas/liquid feeder, and the energy treatment device, and
drive control of the light modulator, the gas/liquid feeder, and the energy treatment device is performed at the image pickup instrument.

5. The medical system according to claim 1, wherein the image pickup signal is a signal obtained by compressing a RAW image signal.

6. The medical system according to claim 1, comprising a plurality of display devices.

7. The medical system according to claim 2, wherein with the second processing specification, processing performed at the second frame rate is divided into a plurality of subframes and the image development processing is performed for each of the subframes.

8. A processing protocol control method comprising:
pairing an image pickup instrument, a signal processing device, and a display device through a communication line including a relay device, the image pickup instrument being configured to output an image pickup signal acquired by picking up an image of an object, the signal processing device being configured to generate an observation image from the image pickup signal, the display device being configured to display the observation image;
deriving, by the signal processing device, a processing sequence that minimizes a time duration from when the image pickup instrument picks up an image of an object until the display device displays the observation image, based on a first processing specification of the image pickup signal at the image pickup instrument, a second processing specification of the signal processing device, a third processing specification of the observation image at the display device, and a communication protocol of the relay device;
providing instruction of a fourth processing specification from the signal processing device to the image pickup instrument based on the processing sequence; and
providing instruction of a fifth processing specification from the signal processing device to the display device based on the processing sequence.

9. The processing protocol control method according to claim 8, wherein the first processing specification is a first frame rate at which the image pickup signal is acquired and a first transmission unit in which the image pickup signal is transmitted, the second processing specification is a second frame rate in image development processing of generating the observation image from the image pickup signal and a start condition of the image development processing, and the third processing specification is a third frame rate in display processing of displaying the observation image and a start condition of the display processing.

10. The processing protocol control method according to claim 9, wherein in the processing sequence, when the first frame rate is lower than the second frame rate, the signal processing device changes a value of the second frame rate to a value of the first frame rate.

11. The processing protocol control method according to claim 9, wherein in the processing sequence, when the second frame rate is lower than the first frame rate, the signal processing device changes a value of the first frame rate to a value of the second frame rate as the fourth processing specification of the image pickup instrument.

12. The processing protocol control method according to claim 9, wherein the processing sequence compares each of the first frame rate, the second frame rate, and the third frame rate with a fourth frame rate that is a communication speed of the relay device, and provides instruction that changes any frame rate higher than the fourth frame rate to a value of the fourth frame rate.

13. The processing protocol control method according to claim 9, wherein in the processing sequence, when the third frame rate is lower than the first frame rate and the second frame rate, the signal processing device changes a value of the first frame rate and a value of the second frame rate to a value of the third frame rate.

14. The processing protocol control method according to claim 8, wherein the image pickup signal is a signal obtained by compressing a RAW image signal.

15. The processing protocol control method according to claim 9, wherein with the second processing specification, processing performed at the second frame rate is divided into a plurality of subframes and the image development processing is performed for each of the subframes.

16. A signal processing device comprising:

a reception circuit configured to receive an image pickup signal from an image pickup instrument through a relay device;

a transmission circuit configured to transmit an observation image to a display device through the relay device;

a memory; and a processor including hardware, wherein the processor detects a first processing specification of the image pickup signal at the image pickup instrument, a second processing specification of the signal processing device, a third processing specification of the observation image at the display device, and a communication protocol of the relay device and stores the first processing specification, the second processing specification, the third processing specification, and the communication protocol in the memory, and derives a processing sequence of a condition that a time duration from when the image pickup instrument picks up an image of an object until the display device displays the observation image is minimized, based on each of the first processing specification, the second processing specification, the third processing specification, and the communication protocol of the relay device, which are stored in the memory, and the signal processing device provides instruction of a fourth processing specification to the image pickup instrument based on the processing sequence and the signal processing device provides instruction of a fifth processing specification to the display device based on the processing sequence.

17. The signal processing device according to claim 16, wherein the first processing specification is a first frame rate at which the image pickup signal is received and a first transmission unit in which the image pickup signal is transmitted, the second processing specification is a second frame rate in image development processing of generating the observation image from the image pickup signal and a start condition of the image development processing, and the third processing specification is a third frame rate in display processing of displaying the observation image and a start condition of the display processing.

18. The signal processing device according to claim 16, wherein the image pickup signal is a signal obtained by compressing a RAW image signal.

19. The signal processing device according to claim 17, wherein with the second processing specification, processing performed at the second frame rate is divided into a plurality of subframes and the image development processing is performed for each of the subframes.

* * * * *